(12) United States Patent
Huang et al.

(10) Patent No.: US 9,586,192 B2
(45) Date of Patent: *Mar. 7, 2017

(54) FUNCTIONALIZED MEDIA AND METHODS OF MAKING AND USING THEREFOR

(71) Applicant: BROWN UNIVERSITY, Providence, RI (US)

(72) Inventors: Yongsong Huang, Barrington, RI (US); James Dillon, Providence, RI (US)

(73) Assignee: BROWN UNIVERSITY, Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/600,296

(22) Filed: Jan. 20, 2015

(65) Prior Publication Data

US 2015/0190780 A1    Jul. 9, 2015

Related U.S. Application Data

(63) Continuation of application No. PCT/US2013/051283, filed on Jul. 19, 2013.

(60) Provisional application No. 61/674,015, filed on Jul. 20, 2012.

(51) Int. Cl.

| | | |
|---|---|---|
| C11B 1/10 | (2006.01) | |
| B01J 20/281 | (2006.01) | |
| B01J 20/289 | (2006.01) | |
| B01J 20/32 | (2006.01) | |
| B01J 20/10 | (2006.01) | |
| A61K 31/695 | (2006.01) | |
| B01D 15/08 | (2006.01) | |
| B01J 20/22 | (2006.01) | |
| B01D 15/38 | (2006.01) | |

(52) U.S. Cl.
CPC ........... *B01J 20/281* (2013.01); *A61K 31/695* (2013.01); *B01D 15/08* (2013.01); *B01J 20/103* (2013.01); *B01J 20/22* (2013.01); *B01J 20/289* (2013.01); *B01J 20/3204* (2013.01); *B01J 20/3219* (2013.01); *B01J 20/3246* (2013.01); *B01J 20/3248* (2013.01); *B01J 20/3261* (2013.01); *B01J 20/3293* (2013.01); *B01D 15/3828* (2013.01)

(58) Field of Classification Search
USPC ............................. 514/63; 210/633, 656, 912
See application file for complete search history.

(56) References Cited

U.S. PATENT DOCUMENTS

| | | |
|---|---|---|
| 5,087,359 A | 2/1992 | Kakodkar et al. |
| 5,108,615 A | 4/1992 | Hosea et al. |
| 5,178,746 A | 1/1993 | Darnall et al. |
| 5,262,018 A | 11/1993 | Meadow et al. |
| 5,667,976 A | 9/1997 | Van Ness et al. |
| 5,706,806 A | 1/1998 | Kissinger |
| 5,766,435 A | 6/1998 | Liao et al. |
| 5,770,388 A | 6/1998 | Vorpahl |
| 5,954,959 A | 9/1999 | Smith et al. |
| 6,248,683 B1 | 6/2001 | Fortier et al. |
| 6,379,556 B1 | 4/2002 | Venkat et al. |
| 6,790,802 B1 | 9/2004 | Sechrist |
| 6,908,873 B2 | 6/2005 | Zhou et al. |
| 7,250,388 B2 | 7/2007 | Burch et al. |
| 7,318,892 B2 | 1/2008 | Connell et al. |
| 7,332,086 B2 | 2/2008 | Sherrington et al. |
| 7,335,306 B2 | 2/2008 | Grant et al. |
| 8,012,350 B1 | 9/2011 | Alam |
| 8,123,041 B2 | 2/2012 | Vladimir |
| 8,403,880 B2 | 3/2013 | Hopping et al. |
| 8,404,091 B2 | 3/2013 | Ding et al. |
| 8,425,780 B2 | 4/2013 | Beiriger |
| 2004/0000523 A1 | 1/2004 | Rosenberg et al. |
| 2005/0119497 A1 | 6/2005 | Hong et al. |
| 2005/0267069 A1 | 12/2005 | Brown et al. |
| 2012/0272791 A1 | 11/2012 | Bai et al. |

FOREIGN PATENT DOCUMENTS

| | | |
|---|---|---|
| WO | 2007073765 A1 | 7/2007 |
| WO | 2012019134 A2 | 2/2012 |
| WO | WO 2012/019134 A2 * | 2/2012 ............ B01J 20/282 |

OTHER PUBLICATIONS

Arai et al. "Arsenic speciation and reactivity in poultry litter" 2003 Environ. Sci. Technol. 37 (18): 4083-4090.
Aveston et al. "Adsorption of Gold from Cyanide Xolutions by Anionic Resins" 1958, Journal of the Chemical Society 231-239.
Baldo et al. "Remote Stripping Analysis of Lead and Copper by a Mercury-Coated Platinum Microelectrode" 2004 Electroanalysis 16 (5): 360-366.
Bannon et al."Anodic stripping voltammetry compared with graphite furnace atomic absorption spectrophotometry for blood lead analysis" 2001 Clin. Chem. 47 (9): 1703-1704.
Burdette et al. "ZP4, an improved neuronal Zn2+ sensor of the Zinpyr family" 2003 J. Am. Chem. Soc. 125 (7), 1778-1787.
Burstall et al. "Ion exchange process for recovery of gold from cyanide solution" 1953 Ind. Eng. Chem. 45: 1648-1658.
Chincilla et al. "Recent advances in Sonogashira reactions" 2011 Chem. Soc. Rev. 40: 5084-5121.
Crudden "Mercaptopropyl-modified mesoporous silica: a remarkable support for the preparation of a reusable, heterogeneous palladium catalyst for coupling reactions" 2005 J. Am. Chem. Soc. 127 (28): 10045-10050.
Darwish et al. "Development and validation of a one-step immunoassay for determination of cadmium in human serum" 2002 Anal. Chem. 74 (1): 52-58.
Eksperiandova et al. "Analysis of waste water by x-ray fluorescence spectrometry" 2002 X-ray Spectrom. 31 (3): 259-263.
Evano et al. "Copper-mediated coupling reactions and their applications in natural products and designed biomolecules synthesis" 2008, Chem Rev. 108: 3054-3131.
Falciola et al. "Copper-Catalyzed Asymmetric Allylic Alkylation" 2008 Eur. J. Org. Chem. 22: 3765-3780.
Fu "The development of versatile methods for palladium-catalyzed coupling reactions of aryl electrophiles through the use of P(t-Bu)3 and PCy3 as ligands" 2008, Acc. Chem. Res. 41: 1555-1564.
Garrett et al. "The Art of Meeting Palladium Specifications in Active Pharmaceutical Ingredients Produced by Pd-Catalyzed Reactions" 2004 Adv. Synth. Catal. 346: 889-900.
Green et al. "Use of Selectiwe Ion Exchange Paper in X-Ray Spectrography and Neutron Activation, Application to the Determination of Gold" 1970 Anal. Chem. 42: 1749-1753.
Godwin "A Selective, Ratiometric Fluorescent Sensor for Pb2+" 2000 J. Am. Chem. Soc. 122 (1): 174-175.

(Continued)

*Primary Examiner* — Pancham Bakshi
(74) *Attorney, Agent, or Firm* — Lawson & Weitzen LLP; Sonia K. Guterman; Preeti T. Arun (57) ABSTRACT

Methods, compositions, devices and kits are provided herein for separating, scavenging, capturing or identifying a metal from a target using a medium or scaffold with a selenium-containing functional group. The medium or the scaffold including the selenium-containing functional group has affinity and specificity to metal ions or compounds having one or more metals, and efficiently separates, recovers, and scavenges of the metals from a target such as a sample, solution, suspension, or mixture.

8 Claims, 3 Drawing Sheets

(56) References Cited

OTHER PUBLICATIONS

Hartwig "Evolution of a fourth generation catalyst for the amination and thioetherification of aryl halides" 2008 Acc. Chem. Res. 41: 1534-1544.

Heck et al. "Palladium-Catalyzed Vinylic Hydrogen Substitution Reactions with Aryl, Benzyl, and Styryl Halides" 1972 J. Org. Chem. 37 (14): 2320-2322.

Kantchev et al. "Palladium complexes of N-heterocyclic carbenes as catalysts for cross-coupling reactions—a synthetic chemist's perspective" 2007 Chem. Int. Ed. 6: 2768-2813.

Knochel et al. "Functionalization of heterocyclic compounds using polyfunctional magnesium and zinc reagents" 2001 J. Org. Chem. 7: 1261-1277.

Knowles. et al. "The Heck-Mizoroki cross-coupling reaction: a mechanistic perspective" 2007 Org. Biomol. Chem. 5: 31-44.

Krief et al. "Synthesis of Selenoacetals" 1985 Tetrahedron. 41(21): 4793-4812.

Liu et al. "Determination of cadmium, mercury and lead in seawater by electrothermal vaporization isotope dilution inductively ively coupled plasma mass spectrometry" 1999 Spectrochim. Acta, Part B 54 (9): 1367-1375.

Lu et al. "New highly sensitive and selective catalytic DNA biosensors for metal ions" 2003 Biosens. Bioelectron. 18 (5-6): 529-540.

Marion et al. "Well-defined N-heterocyclic carbenes-palladium(II) precatalysts for cross-coupling reactions" 2008 Am. Chem. Res. 41: 1440-1449.

Martin et al. "Palladium-catalyzed Suzuki-Miyaura cross-coupling reactions employing dialkylbiaryl phosphine ligands" 2008 Acc. Chem. Res. 41: 1461-1473.

Mingzhong et al. "Silica-supported poly-γ-methylselenopropylsiloxane palladium complex: An efficient catalyst for Heck carbonylation of aryl halides" 2002, Reactive & Functional Polymers. 50 (2) 191-195.

Miyaura "Oraganoboron compounds in cross-coupling reaction" 2002 Top. Curr. Chem. 219: 11-59.

Mizoroki et al. "Arylation of Olefin with Arul Iodide Catalyzed by Palladium" 1971 Bull. Chem. Soc. Jap. 44 (2): 581.

Mlynarz et al. "Impact of the peptide sequence on the coordination abilities of albumin-like tripeptides towards Cu2+, Ni2+ and Zn2+ ions. Potential albumin-like peptide chelators" 2002 New J. Chem. 26 (2): 264-268.

Pettit et. Al "A comparison of the donor properties of group VIB elements" 1967 Chem. Commun. 1179-1180.

Shetty et al. "Whole cell-based sensing systems for metal ions" 2001 Abstr. Pap. Am. Chem. S. 221: U92-U92.

Shults "Modular and tunable chemosensor scaffold for divalent zinc" 2003 J. Am. Chem. Soc. 125 (35): 10591-10597.

Skoog et al. 2006 Principles of Instrumental Analysis (sixth edition) Brooks Cole Publishing chapter 28 (40 pgs.).

Sundberg "Direct Adsorption of Solvent-Extracted Gold on a Chelating Ion Exchange Resin" 1975 Anal. Chem., 47, 2037-2046.

Surry et al. "Dialkylbiaryl Phosphines in Pd-Catalyzed Amination: A User's Guide" 2011 Chem. Sci. 2: 27-50.

Valente et al. "The development of bulky palladium NHC complexes for the most-challenging cross-coupling reactions" 2012 Chem. Int. Ed. 51: 3314-3332.

Wasiak "GC investigation of olefins with chemically bonded gamma-mercaptopropylsilane-copper(II) complexes", 1987 Chromatographia 23(6): 423-426.

Welch, C.J. "Adsorbent Screening for Metal Impurity Removal in Pharmaceutical Process Research" 2005 Org. Process Res. Dev. 9: 198-205.

Welch, C.J. "Adsorbent Screening Using Microplate Spectroscopy for Selective Removal of Colored Impurities from Active Pharmaceutical Intermediates" 2008 Org. Process Res. Dev. 12: 81-87.

Wessjohann et al. "Selenium in chemistry and biochemistry in comparison to sulfur" 2007 Biol. Chem., vol. 388: 997-1006.

Wu et al. "Enzymatically and combinatorially generated array-based polyphenol metal ion sensor" 2000 Biotechnol. Prog. 16 (3): 513-516.

Yang et al. "Sub-ppt detection limits for copper ions with Gly-Gly-His modified electrodes" 2001 Chem. Commun. 19: 1982-1983.

International Search Report and Written Opinion of the International Searching Authority mailed Nov. 6, 2013 in PCT/US13/51283 (13 pages).

* cited by examiner

FUNCTIONALIZED MEDIA AND METHODS OF MAKING AND USING THEREFOR

RELATED APPLICATIONS

This application claims the benefit of International application number PCT/US2013/051283 filed Jul. 19, 2013 which claims the benefit of U.S. provisional application Ser. No. 61/674,015 filed Jul. 20, 2012 entitled, "Functionalized chromatographic materials and methods of making and using therefor" by Yongsong Huang and James Dillon, each of which is incorporated by reference herein in its entirety.

GOVERNMENT FUNDING

This invention was made with government support under grant NNX09AM82G awarded by the National Aeronautics and Space Administration (NASA) Astrobiology and Exobiology, under grant EAR-0902805 awarded by the National Science Foundation (NSF), under grant number NNX10AI95H awarded by the National Space Grant College and Fellowship Program (Rhode Island), and under grant number NNX11AR21A awarded by NASA Experimental Program to Stimulate Competitive Research (EPSCoR) Research and Infrastructure Development. The government has certain rights in the invention.

FIELD OF INVENTION

Media and methods of making and using are provided for reusable, reproducible and efficient capture and separations of metals and/or organic chemicals from a target such as a solution, a suspension, or a mixture.

BACKGROUND

Chromatography is a widely used technique for separating organic and inorganic compounds and substances, e.g., amino acids, proteins, nucleic acids, hydrocarbons, and carbohydrates. Effective chromatography is influenced mainly by efficiency and selectivity of a chromatographic medium with respect to specific compounds of interest. Major improvements in column efficiency can be obtained by using more uniform particle size, or in the case of high performance liquid chromatography (HPLC), decreasing particle size of the packing material. For example in the past years, typical particle size for HPLC has decreased from about ten micrometers (μm or micron) to 1.8 μm, yielding a great increase increased in column efficiency. However, reduction in particle size can be accompanied by higher operating pressures and a need for more sophisticated design and expensive instrumentation such as ultra-high pressure liquid chromatography (UHPLC) systems. See Skoog et al. 1997 Principles of Instrumental Analysis (fifth edition) Brooks Cole Publishing p. 725-743; and Skoog et al. 2006 Principles of Instrumental Analysis (sixth edition) Brooks Cole Publishing chapter 28.

A more effective approach for improving compound resolution is to alter the column selectivity of the chromatographic medium with respect to specific compounds. The packing material for liquid chromatography is commonly based on porous silica particles. The silanol functional groups on the silica surface can be modified by conjugating with a variety of alkyl and other functional groups to change the affinity and selectivity of the packing materials to different compounds. For example, attaching a $C_{18}$ alkyl chain on the silanol group creates so called reversed-phase liquid chromatographic media that are widely used for separating polar organic compounds. Other ways of modifying the resolution properties of silica gel include physically attaching compounds or ions onto the surface of porous silica particles. For example, silver ion ($Ag^+$) has been attached by a process referred to as impregnation onto the silica surface by immersing the silica gel in an aqueous solution of silver nitrate ($AgNO_3$). The silver-imbedded silica gel is used to bind to molecules having electron rich bonds (Zeng et al., international application number PCT/US2011/046810 filed Aug. 5, 2011 which is incorporated by reference herein in its entirety).

While chromatographic media is effective for binding many molecules (e.g., proteins), it would be useful to have media that selectively bind metals or metal compounds. Media that specifically bind metal ions (e.g., silver, platinum, and nickel) and that bind metal-containing molecules are needed for medical, industrial and pharmaceutical applications. Palladium compounds are widely used catalysts for carbon-carbon and carbon-heteroatom coupling reactions (e.g., Heck, Suzuki-Miyaura, Stille, Negishi, and Tsuji-Trost reactions) and are commonly used in pharmaceutical development and production. For the synthesis of pharmaceutical compounds there are strict regulations that require the amount of heavy metals, such as palladium, to be limited to amounts of about two parts per million (ppm) to 20 ppm in the active pharmaceutical ingredient (Garrett, C. E. et al. 2004 Adv. Synth. Catal. 346: 889-900). There is a current need for improved materials and more efficient methods for scavenging, removing or separating metals for example in the synthesis and purification of active pharmaceutical ingredients.

SUMMARY

An aspect of the invention provides a composition for recovering, removing, or scavenging a metal from a target, the composition including: a selenium-containing functional group immobilized or covalently bound to a medium or scaffold, such that the selenium-containing functional group selectively binds to the metal. For example, the metal is a metal of interest located in a fluid or suspension.

In various embodiments of the composition, the metal is selected from at least one of the group consisting of: a toxic metal, a composite metal, a high value metal, a transition metal, a lanthanide metal, and an actinide metal. For example, the metal is at least one selected from the group consisting of: scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, actinium, rutherfordium, dubnium, seaborgium, bohrium, hassium, meitnerium, darmstadtium, and roentgenium. In various embodiments, the metal includes a metal halide, a metal oxide, or a salt thereof. In a related embodiment, the metal includes a catalyst in an organic chemistry reaction. For example, the metal includes a metal component of a catalyst employed in an industrial process.

In a related embodiment, the metal includes a plurality of metals. For example, the plurality of metals includes a class of metals located in the same column in the periodic table, or a class of metals having different bonding affinity to the selenium-containing functional group.

The medium in various embodiments of the composition includes a chromatographic medium. For example, the chromatographic medium forms an analytical component of a system selected from: normal phase, reversed-phase, liquid, planar, column, gravity or flush, flash, thin layer, high performance liquid, and gas chromatography. In various embodiments, the medium or the scaffold is connected to an analytical device, e.g., a computer and a detector, for identifying presence of the metal and/or presence of at least one other component of the target. In various embodiments, the analytical device includes an optical device.

In various embodiments of the composition, the target includes at least one selected from the group of: a solution, a suspension, and a mixture. In related embodiments, the target includes a sample, mixture, compound, solution, suspension, gel, slurry, or solid. For example, the target (e.g., a body or reaction fluid to be treated) has been exposed to a metal or a plurality of metals.

The composition and/or the medium or scaffold in various embodiments include at least one of: a slide, a planar support medium, or a bead. For example the composition and/or the medium or scaffold includes a porous material, e.g., a porous membrane. Alternatively, the composition and/or the medium or scaffold includes a non-porous material. In various embodiments, the composition is useful as a scaffold for scavenging for metal complexes, as a reagent and catalyst support for organic synthesis, as a chromatography media, a capture medium, or a filtration media.

The medium or scaffold in various embodiments includes at least one selected from the group consisting of: silica, silica gel, alumina, polystyrene, agarose, modified polymeric resin, polymer fiber, cellulose, magnesium silicate, dextran, and starch. In a related embodiment, the medium or scaffold includes a substrate or nanoparticle that allows presentation of the selenium-containing functional group to selectively bind to the metal. In various embodiments, the medium or scaffold includes at least one polymer that enhances a surface property of the medium or scaffold, e.g., durability, strength, specificity, and resistance to corrosion or contamination. For example, the at least one polymer (e.g., a polyethylene glycol, a polyelectrolyte, an anionic polymer, and a cationic polymer) reduces non-specific binding of the selenium-containing functional group to non-metal components of the target. In a related embodiment, the polymer strengthens the medium or scaffold against pressures encountered during binding of the metal to the selenium-containing functional group of the composition.

In various embodiments, the medium or the scaffold includes a synthetic or a natural polymeric material. For example, the polymeric material includes a polyolefin such as polyethylenes; a polyethylene; a polypropylene; a polysulfone; a polyvinyl chloride; a polyesters such as a polyethylene terephthalate; a polyamides; a acrylates such as polymethylmethacrylate; a styrenic polymer; and mixtures of any of the above polymeric materials. In various embodiments, the synthetic material includes a cellulose, an epoxy, an urethane, and the like.

In various embodiments, the selenium-containing functional group includes or is linked to the medium by at least one spacer selected from the group of: a sulfur-containing functional group: $(C_1-C_{30})$alkyl, $(C_1-C_{30})$alkynyl, $(C_3-C_{12})$ carbocyclyl, $(C_1-C_{30})$alkoxy, $(C_1-C_{30})$heteroalkyl, $(C_6-C_{30})$ aryl, $(C_1-C_{30})$heteroaryl, and $(C_6-C_{30})$aryl$(C_1-C_{30})$alkyl. For example, the selenium-containing functional group includes or is linked to the medium by at least one spacer selected from the group consisting of: a sulfur-containing functional group: $(C_1-C_{18})$alkyl, $(C_1-C_{18})$alkoxy, $(C_1-C_{18})$ heteroalkyl, $(C_6-C_{10})$aryl, $(C_1-C_9)$heteroaryl, and $(C_6-C_{10})$ aryl$(C_1-C_6)$alkyl. For example, the spacer includes a carbocycl, a perhaloalkyl, an alkenyl, a heterocyclyl, a heteroaryl, a heteroaralkyl, a substituted amino (e.g., mono-substituted and di-substituted), a sulfonyl, a sulfinyl, an acyl, a boronyl, a propyl group, or a benzyl group. In various embodiments, the selenium functional group includes an electron-donating moiety for example an ether. In various embodiments, the medium and/or the spacer comprises at least one protecting group.

The composition in various embodiments forms an analytical component of a chromatography system selected from: normal phase, reversed-phase, liquid, planar, column, flush, flash, thin layer, high performance liquid, gas, and solid phase extraction chromatography. The composition in a related embodiment forms a component of a dialysis system. In a related embodiment, the composition is used in an organic chemistry reaction scheme to capture or remove the metal from a reagent and/or a product. For example, the composition is used to scavenge, recover, or remove a platinum catalyst or a rhodium catalyst. In various embodiments, the metal is a high value metal used in organic chemistry synthesis or cell culture processing.

The selenium-containing functional group in various embodiments effectively separates the metal from at least one of: a sample, suspension, a solution, or a reaction mixture. For example, the sample includes a biological sample. In various embodiments, the biological sample is urine, saliva, lymph, an excretion, blood, or serum. In various embodiments, the reaction mixture includes an active pharmaceutical ingredient (API) or an active ingredient. In various embodiments, the reaction mixture is an organic chemistry reaction mixture, for example a mixture produced by a hydrogenation reaction or a coupling reaction. For example, the coupling reaction includes a Heck, Suzuki-Miyaura, Stille, Negishi, or Tsuji-Trost reaction. In various embodiments, the reaction mixture includes the metal which includes a metal catalyst. For example, the metal is a residual metal catalyst from a chemical reaction.

The selenium-containing functional group in various embodiments separates the metal from at least one compound or metal having a different atomic mass. Alternatively, the selenium-containing functional group separates the metal from at least one other metal having a different oxidation state, for example an oxidation state of zero, +1, +2, +3, or +4.

The selenium-containing functional group in various embodiments of the composition includes a selenolate or a selenol, for example the selenol includes a benzylesterselenol trimethoxysilane, a propylselenol trimethoxysilane, a derivative, or a homolog thereof. In various embodiments, the selenium-containing functional group includes an electron-donating moiety, such as an ether, that enhances binding of the selenium-containing functional group to the metal.

An aspect of the invention provides a method for recovering, removing, or scavenging a metal from a target, the method including: contacting the target containing the metal with a medium or a scaffold including a selenium-containing functional group, such that the selenium-containing functional group specifically binds to the metal and separates the metal from at least one remaining component in the target.

The metal in various embodiments of the method is selected from the group of: a toxic metal, a composite metal, a high value metal, a transition metal, a lanthanide metal, and an actinide metal. For example the metal is at least one selected from the group of: scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, actinium, rutherfordium, dubnium, seaborgium, bohrium, hassium, meitnerium, darmstadtium, and roentgenium. In various embodiments, the metal is a catalyst in a chemical reaction.

The medium or the scaffold in various embodiments of the method includes a silica, a polymer material (e.g., an acrylate and a polyamide), a fiber, and a glass. In a related embodiment, the medium includes an activated silica, for example an activated silica gel. In various embodiments, the medium or the scaffold is selected from the group consisting of: a silica; a silica gel; an alumina; a polystyrene; an agarose; a resin for example a modified polymeric resin; a cellulose; a magnesium silicate; dextran; and starch.

In a related embodiment, the medium or the scaffold includes a porous material. Alternatively, the medium or the scaffold includes a non-porous material. In various embodiments of the method, the medium or the scaffold includes a planar medium or a bead. In various embodiments, contacting includes dialyzing the target, which is a sample from a subject. In various embodiments, the method includes, after contacting, analyzing the metal and/or the remaining components of the target, which is a sample not from a subject, e.g., a sediment or soil sample, a water sample, a core sample, and a petroleum-derived sample.

The method further includes in various embodiments separating the medium or the scaffold from the target, such that the target is a material, for example an aqueous or liquid material, a reaction mixture, a complex material, or a biological sample. In various embodiments, the method further includes, prior to contacting, synthesizing or collecting the target.

In various embodiments of the method, contacting further includes at least one step selected from the group of: stirring, mixing, agitating, sonicating, and filtering. For example stirring or sonicating involves enhancing interaction between the target and the metal or the scaffold to increase binding of the selenium-containing functional group to the metal. In various embodiments of the method, contacting is performed at room temperature. In various embodiments of the method, contacting is performed below room temperature or above room temperature. For example, the temperature during contacting is raised above room temperature to enhance binding of the selenium-containing functional group to the metal.

In various embodiments contacting is performed over a period of time or during an incubation or residence period sufficient to effectively bind the metal to the selenium-containing functional group. For example, the period of time may be minutes, hours, or days.

In various embodiments of the method, the target including the metal is in a reaction mixture container, and contacting is performed in the container. In various embodiments, contacting is performed by applying the target to the medium or scaffold (e.g., a column) containing the selenium-containing functional group. Alternatively, contacting is performed by administering the medium or scaffold (e.g., a bead) containing the selenium-containing functional group to the target. For example, the medium or scaffold is administered to the target contained in a container or vessel. In various embodiments, contacting is performed using or in a fluid. For example, the fluid is at least one solvent, solution, or a gas. In various embodiments, contacting is performed in an aqueous solution, for example the solution is at about pH 2 to about pH 12. For example, contacting is performed using an organic solvent or an organic solution.

In various embodiments, contacting includes adding an effective amount of the medium or the scaffold. For example, the effective amount is a ratio of amount or moles of the medium or the scaffold containing the selenium-containing functional group compared to amount or moles of the metal. In general, the ratio is optimized for the type of selenium-containing functional group used or for the specific metal to be capture, removed, or scavenged. In various embodiments, the ratio is at least: about 1:1 to about 2:1, about 2:1 to about 6:1, about 6:1 to about 10:1, about 10:1 to about 20:1, about 20:1 to about 30:1, about 30:1 to about 40:1, about 40:1 to about 50:1, about 50:1 to about 60:1. For example, the ratio is at least about 1:1 to about 2:1, about 2:1 to about 4:1, about 4:1 to about 6:1, about 6:1 to about 8:1, about 8:1 to about 10:1, about 10:1 to about 12:1, and about 12:1 to about 15:1.

In various embodiments, the composition comprises a plurality of selenium-containing functional groups that bind to and/or complex the metal (e.g., metal atom or metal compound). For example, the composition includes at least two distinct selenium-containing functional groups. For example, the composition includes a selenoether functional group and a selenobenzyl functional group.

In various embodiments, after contacting, the method further includes washing or drying a resulting solid. For example the resulting solid includes an organic chemistry reaction product containing at least one contaminant, material, or catalyst.

In related embodiments of the method, contacting includes a step of using or adding at least one solvent selected from the group consisting of: chloroform, dichloromethane, ethyl acetate, diethyl ether, acetic acid, hexane, toluene, ethanol, acetone, methanol, tetrahydrofuran, dimethyl sulfoxide, acetonitrile, and a combination thereof.

The medium or the scaffold in various embodiments of the method is covalently linked or immobilized to the selenium-containing functional group by at least one spacer. Alternatively, in various embodiments the medium or the scaffold is attached or embedded with the selenium-containing functional group. In various embodiments of the method, the spacer is selected from the group consisting of: $(C_1-C_{18})$alkyl, $(C_1-C_{18})$alkoxy, $(C_1-C_{18})$heteroalkyl, $(C_6-C_{10})$aryl, $(C_1-C_9)$heteroaryl, and $(C_6-C_{10})$aryl$(C_1-C_6)$alkyl. In various embodiments, the spacer reduces steric hindrance.

In various embodiments, the selenium-containing functional group is linked to the medium or the scaffold by a sulfur-containing functional group, for example a thiol or a thiolate. In various embodiments, the medium or scaffold further includes a sulfur-containing functional group that is not directed linked to the selenium-containing functional group.

In various embodiments, prior to contacting, the method includes reacting a selenium material (e.g., a selenium benzyl ester) with at least one silane. In various embodiments, the silane is selected from: 3-mercaptopropyltrimethoxysilane, 3-hydroxypropyltrimethoxysilane, 3-glycidoxypropyltrimethoxysilane, n-butyltrimethoxysilane, and 3-cyanopropyltrimethoxysilane. For example, reacting involves any reaction shown in FIGS. 1 and 3-4.

In various embodiments, the method further includes, after contacting, analyzing presence of the metal in the target. In various embodiments, analyzing includes detecting at least one absorbance, or performing mass spectrometry. In various embodiments, analyzing further includes determining the identity of the at least one remaining component in the target. For example, the at least one remaining component is selected from the group of: a protein, a peptide, a carbohydrate, and a genetic material (e.g., DNA and RNA). In various embodiments, the at least one remaining component and/or target includes at least one selected from the group consisting of: a hydrocarbon, an alkene, an alkenone, a triglyceride, a cyclic compound, a monoglyceride, a diglyceride, a wax ester, a steryl ester, a phthalate, a sterol, a steroid, a terpene, a terpenoid, a triterpernoid, a fatty acid, a lipid including a phospholipid and other complex lipid molecules, an oil, a sugar, an oligosaccharide, a polysaccharide, a carbohydrate, a protein, an amino acid, a fossil fuel, a natural compound, a synthetic organic compound, a petroleum-derived compound, a coal-derived compound, and a combination thereof found in a biological sample or an environmental sample.

In various embodiments, the method further includes, after contacting, removing at least one non-metal component of the target from the target and/or removing the metal bound to the selenium-containing function group from the target. For example, removing includes discarding the metal. In various embodiments, removing includes administering a fluid or a solid to the medium or scaffold including the selenium-containing function group. For example, the fluid is an acid. In various embodiments, the acid is an inorganic acid. Alternatively, the acid includes an organic acid for example an oxalic acid. In various embodiments, the acid includes at least one of: hydrofluoric acid (HF), hydrochloric acid (HCl), hydrobromic acid (HBr), hydroiodic acid (HI) hypochlorous acid (HClO), chlorous acid ($HClO_2$), chloric acid ($HClO_3$), perchloric acid ($HClO_4$), hydrobromic acid (HBR), hydroiodic acid (HI), sulfuric acid, ($H_2SO_4$), fluorosulfuric acid ($HSO_3F$), nitric acid ($HNO_3$), phosphoric acid ($H_3PO_4$), fluoroantimonic acid ($HSbF_6$), fluoroboric acid ($HBF_4$), hexafluorophosphoric acid ($HPF_6$), chromic acid ($H_2CrO_4$), boric acid ($H_3BO_3$), and a sulfonic acid (e.g., methanesulfonic acid, p-toluenesulfonic acid, trifluoromethanesulfonic acid, or a derivative, homolog, or analog thereof. In various embodiments, the acid includes a hydrogen halide, a halogen oxoacid, an organic acid including a carboxylic acid (e.g., acetic acid, citric acid, formic acid, and oxalic acid), or a derivative, homolog, or analog thereof. In various embodiments, the fluid or the solid disrupts the binding of the metal to the selenium-containing function group. In various embodiments, the fluid or the solid includes an oxidizing agent, e.g., hydrogen peroxide, nitrous oxide, and a perchlorate. In various embodiments, removing includes administering an organo-metallic complexing agent or a flocculating agent.

In various embodiments of the method, removing includes using at least one of: acetone; ethanol; hexamethylphosphoramide (HMPA); methanol; N,N-dimethylformamide; acetonitrile; dimethylsulfoxide (DMSO); nitromethane; N-methylpyrrolidone (NMP); formic acid; sulphuric acid; water; a glycol, a halogenated solvents (e.g., chloroform, dichloromethane, trichloroethylene); and the like. In various embodiments of the method, removing the metal includes using at least one of: an ether; an alcohol; an amine; an amide; tetrahydrofuran (THF); a dioxanne; an ethylacetate; a pyridine; formic acid; acetic acid; propionic acid; an alkane; an aromatic (e.g., benzene, toluene, xylenes, and mesitylene); or a derivative, a homolog, or a analog of any thereof.

In various embodiments, removing includes drying or heating the medium or the scaffold, e.g., raising the temperature to a melting point of the metal or the composition, or raising the temperature to a boiling point of the target in solution.

In various embodiments, removing includes directing wavelengths of energy (e.g., microwaves and radiation) to the medium or the scaffold, or using magnetic material (e.g., magnetic beads). In various embodiments, removing includes separating by size. In various embodiments, removing includes applying a fluid (e.g., a gas or a liquid) to elute or collect material in the target that does not bind selenium-containing function group.

In various embodiments, the method further includes, after contacting, treating or recharging the medium or the scaffold including the selenium-containing functional group, such that the medium or the scaffold can be re-used. In various embodiments, treating or recharging includes administering a fluid to the medium or the scaffold. For example, the fluid comprises an acid or an oxidizing agent. In various embodiments of the method, treating or recharging includes applying a wash fluid to the medium or the scaffold. For example, the wash solution removes the metal and/or an molecules or compounds (e.g., genetic material, protein, peptide, carbohydrate, drug for example a small molecule drug) from the medium or scaffold.

An aspect of the invention provides a kit for recovering, removing, or scavenging a metal from a target, the kit containing: a composition including a selenium-containing functional group immobilized or covalently bound to a medium, such that the selenium-containing functional group selectively binds to the metal; and, a container. In various embodiments, the composition is a capture medium for scavenging the metal which is a metal catalyst.

In various embodiments, the medium includes a chromatographic medium or a bead. In various embodiments of the kit, the medium is selected from the group consisting of: silica gel, alumina, polystyrene, agarose, modified polymeric resin, cellulose, magnesium silicate, dextran, and starch. In various embodiments, the medium or the scaffold includes a tube and/or is a component of a dialysis system. For example the tube and/or dialysis system is sterile.

In various embodiments, the kit further includes instructions for use. For example, the instructions are a method for making the composition, or a method for recovering, removing, or scavenging the metal from the target using the composition. In various embodiments, the composition is any described in the claims and the specification herein.

In various embodiments of the kit, the metal is selected from the group of: a toxic metal, a composite metal, a high value metal, a transition metal, a lanthanide metal, and an actinide metal. In various embodiments, the metal is naturally found in the subject (e.g. iron, cobalt, and chromium). In a related embodiment the metal is found at an excess amount/level that produces a negative effect in a subject. For example, the excess amount/level is due to a natural condition (e.g., hemochromatosis) or due to an environment exposure or contact (e.g., lead paint, chromium dust) or due to ingestion, e.g., contaminated water and food. In various embodiments of the kit, the metal is at least one selected from the group of: scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, actinium, rutherfordium, dubnium, seaborgium, bohrium, hassium, meitnerium, darmstadtium, and roentgenium.

An aspect of the invention provides a method for treating a subject exposed to at least one toxic metal, the method including: contacting the subject with an atoxic composition containing: a selenium-containing functional group and a medium attached to the selenium-containing functional group that specifically binds with high affinity to the metal; and removing from the subject a complex of the metal bound to the composition and treating the subject. In various embodiments, the contacting and/or removing is extracorporeal.

The metal in various embodiments of the method is selected from the group of: a composite metal, a high value metal, a transition metal, a lanthanide metal, and an actinide metal. For example, the method includes, prior to contacting, synthesizing the target. In various embodiments, the synthesizing includes using a catalyst in an organic chemistry reaction.

In various embodiments, the composition is compounded/formed in at least one form selected from the group consisting of: a capsule, a tablet, a pill, a powder, a granule, a tubing, a solution, a suspension, and a suppository. For example, the composition is compounded to be porous. In various embodiments, the contacting includes performing dialysis, e.g., hemofiltration or hemodialysis. In various embodiments, the composition is a non-porous. In various embodiments, the composition is formed as a dressing or gauze.

In various embodiments of the method, the method includes, prior to contacting, removing a fluid (e.g., blood) from the subject, and dialyzing the fluid. For example, dialyzing involves using a dialysis assembly including for example at least one tube or dialysis tube, filter membrane, or dialysis fluid. In various embodiments, the method further includes, after dialyzing, reintroducing a resulting dialyzed (i.e., filtered) fluid to the subject, such that the dialyzed fluid lacks harmful or toxic molecules or ions (e.g., metal ions).

The method further includes, after removing, detecting decreased presence of the metal in the subject or from a sample obtained from the subject. In various embodiments, the method further includes identifying a reduction in at least one pathology symptom associated with the exposure to the metal. For example the pathology symptom or an indicium of exposure to the metal is selected from: diarrhea, vomiting, breathing difficulty, fever, inflammation, skin rashes or lesions, bleeding, pain, numbness, loss of consciousness, tissue necrosis, dermatitis, asthma, conjunctivitis, keratitis, ulceration, and organ failure. For example, the subject is a patient suspected of metal poisoning, or a patient having renal failure. In various embodiments, the method includes, prior to contacting, selecting the subject exposed or suspected of exposure to the at least one toxic metal.

The method in various embodiments further includes measuring a reduced amount of the metal in a sample from the subject compared to a control sample obtained prior to contacting. In various embodiments, detecting, measuring, or identifying involves at least one technique or system selected from the group consisting of: electrophoresis, chromatography, immunoblotting, an assay (e.g., ELISA), absorbance detection, and mass spectrometry.

The selenium-containing functional group in various embodiments includes a selenolate or a selenol, for example a benzylesterselenol trimethoxysilane or a propylselenol, trimethoxysilane.

In various embodiments of the method, contacting the subject includes administering the composition by a route selected from at least one of the group consisting of: intramuscular, subcutaneous, intraperitoneal, intradermal, sublingual, intranasal, oral, and by dialysis. For example, blood from the subject is introduced into a dialysis system including the composition for filtration of the metal such that the filtered blood is re-introduced to the subject. In various embodiments, the method further includes, after removing, administering a therapeutic agent, e.g., a drug, a protein, a peptide, a carbohydrate, and a genetic material.

In various embodiments, removing the metal using the composition separates the metal from at least one compound or other metal having a different atomic mass. In various embodiments, removing the metal using the composition separates the metal from at least one other metal having a different oxidation state.

The composition in various embodiments of the method is any of the compositions containing the selenium-containing functional group described herein.

An aspect of the invention provides a device including the composition according to any of claims and in any embodiment described herein. The composition in the device includes any of the compositions including a selenium-containing functional group described herein. For example, the functional group is immobilized or covalently bound to a medium, a support, a membrane, or a scaffold. For example, the device includes a dialysis device or a chromatographic device. In various embodiments, the device includes a solid phase extraction tube. In various embodiments, the device includes a cartridge, a bead, or a column. For example, the device is useful as a capture media. In various embodiments, the device includes a point-of-care device.

In various embodiments, the device is re-usable. For example, the device including the composition comprising the selenium-containing functional group is used to bind to a metal, and is then contacted with a fluid to remove the metal from the selenium-containing functional group. Alternatively, the device in various embodiments is disposable.

An aspect of the invention provides use of a composition according to any of the claims and the embodiments described herein, for manufacture of a device for use in the treatment or prevention of a condition associated with presence of metals in a cell, a tissue, or a fluid of a subject. In various embodiments, the condition is metal poisoning. In various embodiments of the use, the device is for veterinary treatment.

An aspect of the invention provides use of a composition, according to any of claims and embodiments described herein, in a screening assay for the identification of a drug, a therapeutic agent, or a vaccine. For example, the screening assay is performed after an organic chemistry reaction including a catalyst that comprises the metal.

An aspect of the invention provides a method for making a material for separating, capture or identifying metals, the method including: reacting a medium with a selenium-containing functional group such that the functional group covalently binds the metal, thereby forming the material for separating, capturing or identifying the metal. An exemplary method includes a reaction shown in FIGS. 1 and 3-4.

In various embodiments, the method further includes stirring, sonicating or filtering a resulting solid formed by contacting the medium to the selenium-containing functional group. In various embodiments, the method further includes at least one of washing and drying the resulting solid. For example, washing involves using at least one fluid or solvent selected from the group consisting of: chloroform, dichloromethane, ethyl acetate, diethyl ether, acetic acid, hexane, toluene, ethanol, acetone, methanol, tetrahydrofuran, dimethyl sulfoxide, acetonitrile, and a combination thereof. For example, the washing includes using a solution which is a mixture of at least two fluids or solvents.

In various embodiments of the method, the metal is selected from the group consisting of: silver, copper, gold, mercury, cadmium, zinc, nickel, rhodium, palladium, platinum, and a combination thereof.

In various embodiments, the metal includes a metal catalyst, for example a platinum. In various embodiments of the method, reacting the medium with the selenium-containing functional group includes covalently linking or attaching the selenium-containing functional group by at least one spacer, for example the spacer is selected from the group consisting of: $(C_1-C_{18})$alkyl, $(C_1-C_{18})$alkoxy, $(C_1-C_{18})$heteroalkyl, $(C_6-C_{10})$aryl, $(C_1-C_9)$heteroaryl, and a $(C_6-C_{10})$aryl$(C_1-C_6)$alkyl.

In various embodiments of the method, the medium is selected from the group consisting of: silica, a silica gel, alumina, polystyrene, agarose, modified polymeric resin, cellulose, magnesium silicate, dextran, and starch.

An aspect of the invention provides a method of capturing a metal from a target such as a mixture or a fluid, the method including: contacting the target to a composition including a selenium-containing functional group, such that the selenium-containing functional group selectively binds to and captures the metal. The composition in various embodiments is a medium, membrane or scaffold, such that contacting includes applying the target to the composition. For example contacting is performed by adding the medium, the membrane, or the scaffold to the target, or by loading or injecting onto or flowing the target through the medium, the membrane or the scaffold. For example, the membrane is a porous polymer membrane that allows interaction between the polymer and the target in solution. In various embodiments, the medium or the scaffold comprises a bead or polymer material. Alternatively, contacting is performed by adding or applying the composition to the target.

In various embodiments, the method further involves, prior to contacting, synthesizing or producing the target. For example, synthesizing involves performing a chemical reaction with the metal which is used to catalyze the reaction. For example, the metal catalyst is used in a hydrogenation or combination reaction. The metal in various embodiments is platinum, palladium, gold, or other metal suitable for catalyzing the reaction. For example, the metal may be used to scavenge residual metal catalyst from an process fluid or chemical reaction.

The method in various embodiments further includes, after contacting, separating at least one non-metal component of the target from the composition having the bound metal. For example, separating includes collecting or discarding the target, which contains negligible or undetectable amounts of the metal. In various embodiments, the metal has been completely removed from the target. In various embodiments, separating and/or collecting the non-metal component of the target thereby leaves the metal bound to the selenium-containing functional group of composition.

The method in various embodiments further includes analyzing or detecting the metal bound to selenium-functional group of the composition. Analyzing is performed in various embodiments in the context of environment analysis, toxicity diagnosis in fluid from a subject, purification of a pharmaceutical, etc. The method further includes determining presence or amount of the metal bound to selenium-functional group. Determining involves for example removing the metal from the selenium-functional group for example by applying a fluid or agent (e.g., an acid, an oxidizer, or a competing metal-containing compound) that disrupts the binding between the metal and the selenium-functional group. In various embodiments removing involves heating the composition for example to a temperature that selectively melts or dissociates the composition from the metal.

In various embodiments, determining the presence or amount of the metal may be effected using spectrometry, absorbance, transmittance, colorimetry, spectroscopy, or micro (chemical) quantitative analysis. In various embodiments, analyzing involves at least one of the following techniques or procedures: atomic absorption spectrometry, inductively coupled plasma mass spectrometry, anodic stripping voltammetry, or X-ray fluorescence spectrometry. In various embodiments, the target is a fluid from the subject, and analyzing comprises diagnosing or prognosing a medication condition in the subject. For example, the medical condition is metal poisoning or hemochromatosis.

BRIEF DESCRIPTION OF DRAWINGS

FIG. 1 panel A is a drawing of a chemical reaction for synthesizing a propylselenol trimethoxysilane. The chemical reaction shows reacting a bromopropyltrimethoxysilane with potassium selenocyanate (KSeCN) in acetone, and then sodium borohydride ($NaBH_4$) in ethanol to yield a selenol silane.

FIG. 1 panel B is a drawing of a chemical reaction for synthesizing a benzylesterselenol trimethoxysilane. The chemical reaction involves reacting 3-hydroxypropyltrimethoxysilane with a selenium benzyl ester under acidic conditions to yield a selenol silane with an aromatic ring.

DETAILED DESCRIPTION

Use of ion-exchange resins for the removal of metal ions from aqueous solutions is commercially wide spread especially in water softening applications and for the removal of toxic products from effluents. Processing of radioactive wastes, the purification of rare earth metals and the analysis of geological samples are other important activities that involve removal of metal ions. The high cost of available resins and the lack of resin selectivity are major obstacles to separation of metals (Hodgkin et al., U.S. Pat. No. 4,762,556 issued Aug. 9, 1988). Metal catalyzed reactions are commonly used in the manufacture of active pharmaceutical ingredients and fine chemicals, and steps are taken to remove metals from reaction mixtures (Crudden, C. M. 2005 J. Am. Chem. Soc. 127 (28): 10045-10050; Welsh, C. J.

2005 Org. Process Res. Dev. 9: 198-205; and Welch, C. J. 2008 Org. Process Res. Dev. 12: 81-87). The regulatory limits for metal content are becoming increasingly more stringent, for example, United States and European government regulations require candidate drugs and reaction mixtures to have very low concentration levels for many metal ions, e.g., palladium, platinum, copper, mercury, silver and lead. For example the regulations in many cases require metals to be present at amounts of parts per million or parts per billion.

Selective chelating resins have become available commercially, for example resins containing imidodiacetic acid, ethylenediaminetetraacetic acid (EDTA), or picolylamine have been used (Meadow et al., U.S. Pat. No. 5,262,018 issued Nov. 16, 1993; Hosea et al., U.S. Pat. No. 5,108,615 issued Apr. 28, 1992; and Darnall et al., U.S. Pat. No. 5,178,746 issued Jan. 12, 1993). However, these resins are only marginally selective for a particular heavy metal ion and require complex procedures to effect practical separations in commercial situations.

Scavenging of high value metals such as gold has always been of interest for commercial and analytical reasons and many resin systems have been designed to accomplish this. A common polymer used has been the Srafion NMRR resin (Ayalon Water Conditioning Co. Ltd., Haifa, Israel) which has an aromatic sulphaguanidine structure. Although this polymer has good capacity for gold in acidic solutions (greater than five millimoles per gram) it absorbs most other heavy metals as well (Geen, T. E. et al. 1970 Anal. Chem. 42: 1749-1753). Another commonly used analytical resin has been the iminodiacetic acid chelating resin. Although the iminodiacetic resins can be used relatively selectively in some cases, the resins adsorb many other metals as well (L. L. Sundberg 1975 Anal. Chem., 47, 2037-2046). Thus, the possibility for these resins for selectively binding metals is limited.

Many commercially available metal scavengers are produced by cross-linking polystyrene or another polymer, which is expensive. Large scale commercial applications, in which gold would advantageously be recovered by burning off the resin, involve costs that are prohibitive. In these cases a common anion exchange resin such as Amberlite IRA 400 (Dow Chemical; Center Midland, Mich.) is used to recover metals or metal halides. See Venkat et al., U.S. Pat. No. 6,379,556 issued Apr. 30, 2002. These materials are generally not selective, consequently recovery of pure gold from them requires a complex series of selective elutions to remove other metals (Burstall, F. H. et al. 1953 Ind. Eng. Chem. 45: 1648-1658). The capacity of these resins is also not very high, being about one to two millimoles of gold per gram of resin. More selective weak base resins have been produced, however capacity of these is much lower and the resins suffer from interference from sulphur-containing anions (Aveston, J et al. 1958 Journal of Applied Chemistry 8: 77-86). Combinations of weak and strong base resins have also been tried with no significant advantage (Aveston, J. et al. 1958 Journal of the Chemical Society 231-239).

The compositions, methods, kits and devices herein contain a medium that has a selenium atom or selenium-containing functional group that effectively binds to metal and metal compounds. Without being limited by any particular theory or mechanism of action, it is here envisioned that the systems, methods, compositions and kits described herein having a medium with a selenium atom are more effective at binding and/or scavenging a metal than a sulfur atom. The metal is effectively attracted or bound to the selenium atom and does not leach from the stationary phase of the medium into the mobile phase of the solvents. Thus, the compositions, methods, kits and devices herein create a substantially permanent, reusable chromatographic medium for methods to calibrate, discriminate and separate metals from a broad variety of different samples, compounds and analytes having a metal atom and related materials. For example, the sample, compound or the analyte contacted with the selenium-containing functional group, and the sample contains any of a toxic metal, a composite metal, a high value metal, a transition metal, a lanthanide metal, or an actinide metal. In various embodiments, the metal is a catalyst such as a platinum. In various embodiments, the metal is at least one selected from the group of: scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, actinium, rutherfordium, dubnium, seaborgium, bohrium, hassium, meitnerium, darmstadtium, and roentgenium.

Methods and compositions which are media that remove or scavenge metals from a target such as an aqueous solution or a reaction mixture are shown in Examples herein. In various embodiments the chromatographic media described herein are used for many kinds of liquid chromatographic methods including conventional liquid chromatography, HPLC, thin layer chromatography (TLC). An HPLC column described herein is composed of a selenium-containing functional group stationary phase and is used for the separation of metals from samples. The columns containing the media described herein can be repeatedly used for this type of separation, and are shown to maintain the same retention times for these metals. The selenol chromatographic media can be repeatedly tested over a period of time, and show no loss of metal-retention and no change of retention times. The separation is thus highly reproducible and highly stable. The media including the selenium-containing functional group can be safely stored at temperatures below, at or above room temperature with no appreciable physical signs of decomposition or degradation, such as a change in coloration, smell or complexion.

An aspect of the invention provides a chromatographic medium that includes a selenium-containing functional group (e.g. a selenoate) covalently linked or attached to the medium, such that the selenium-containing functional group specifically binds to an atom of a transition metal, by which the chromatographic medium has affinity and specificity to bind a compound, mixture, solution or material having the metal. The phrase "selenolate chromatographic medium" is used interchangeably herein with the phrase "selenium chromatographic medium".

Thiol-functionalized silica gel has not previously been prepared for chromatographic purposes, but has been used for scavenging metal ions from aqueous solutions (Wasiak, W. 1987 Chromatographia 23: 423-426; Huang et al., PCT/US2011/46810 filed Aug. 5, 2011, each of which is incorporated by reference herein in its entirety). Several manufacturers supply thiol-functionalized silica gel (for example, Silicycle; Quebec, Canada). Most manufacturers do not use chromatographic grade silica gel to reduce the cost of production, hence directly purchased thiol-functionalized silica gel may not meet the requirement for liquid chromatography.

Methods of preparation in the Examples herein used high grade chromatographic silica gel, on which modifications were performed including selenol- and propyl-selenol-functionalization. Selenium content in products was carefully monitored to develop at an optimal condition for making selenium-functionalized silica gel. Methods and procedures of use of the media were developed herein to quantitatively bond metal ions (e.g., platinum) onto the selenium-functionalized silica gel. The metal ion was observed to be bonded onto the selenium to form a stable metal-selenium complex so that effective chromatographic separations was successfully performed.

Materials and methods herein involve covalently bonding selenium atoms and/or selenium functional groups to a medium or scaffold (e.g., silica gel), to obtain a chromatographic medium for effective separation of metals from at least one other component, compounds or molecules present in a target sample. Organoselenium compounds in various embodiments form a more stable complex with metals (e.g., silver (I)) in reactions and biological processes than organosulfur compounds (Pettit, L. D. et. al 1967 Chem. Commun. 1179-1180 and Wessjohann, L. A. et al. 2007 Biol. Chem., vol. 388: 997-1006, each of which is incorporated herein by reference in its entirety). Methods are provided herein for producing selenium chromatographic media for separating and identifying metals. Systems, compositions, devices, methods and kits using chromatographic functionalized media are provided herein.

Without being limited by any particular theory or mechanism of action, it is here envisioned that the systems, methods, compositions and kits described herein having a medium or scaffold with a selenium bound to an electron-donating moiety are effective to bind and/or scavenge a metal. In various embodiments, the selenium includes a selenium atom or a selenium functional group, e.g., a selenol. In various embodiments, a composition containing the selenium is used as a capture medium for effectively binding to and capturing a metal.

In various embodiments, the organoselenium functionalized medium or scaffold described herein includes a functional group and/or a substituent that is bound to the selenium. In various embodiments, the functional group and/or the substituent is an electron-donating moiety that enhances binding of the selenium to a metal. In various embodiments, the electron donating moiety includes: a hydrogen, a halogen, a hydroxyl, an amino, an alkyl, an alkoxy, a thioalkyl, an alkylamino, an imine, an amide, a phosphate, a phosphine, a carbonyl, a carboxyl, a silyl, an ether (e.g., a thioether), a sulfonyl, or a ketone. In various embodiments, the alkoxy includes an alkyether or an alcohol. For example, the selenium functionalized medium or scaffold includes a selenoether, or a homolog or analog thereof. The selenoether moiety includes in various embodiments a central selenium atom connected to two alkyl substituents. In various embodiments, at least one of the alkyl substituent is an sp3 (tetrahedral) hybridized carbon atom. The selenoether functionalized medium or scaffold effectively binds or scavenges the metal.

Selenoethers are commonly used to prepare olefinically unsaturated compounds, and have been used as polymeric catalysts for Mizoroki-Heck chemical reactions (Mizoroki, T. et al. 1971 Bull. Chem. Soc. Jap. 44 (2): 581; Heck, R. F. et al. 1972 J. Org. Chem. 37 (14): 2320-2322; Krou, U.S. Pat. No. 4,601,860 issued Jul. 22, 1986; Chung et al., U.S. patent publication number 20050119497 published Jun. 2, 2005; Heyda, international patent publication number WO/2007/073765 published Jul. 5, 2007, each of which is incorporated by reference in its entirety). For example, a poly-γ-methylselenopropylsiloxane catalyst was synthesized by immobilizing chloropropyltriethoxysilane on silica, and reacting the silica with sodium methylselenolate and then with palladium chloride. The selenoether silica is a heterogeneous catalyst for carbonylation of aryl halides (Mingzhonga, C. et al. 2002 Reactive & Functional Polymers. 50:191-195).

A selenolate-functionalized silica gel was synthesized and used in Examples herein to effectively separate metals from solutions, suspensions and mixtures. The attachment between the metal and the selenolate-functionalized silica was observed to be extremely stable, a feature which reduces or even eliminates the possibility of metal leaching.

The effectiveness of the selenolate-functionalized silica to bind to metals such as platinum and silver is shown in Examples herein. It is envisioned that in addition to these metals, other metals such as transition metals are bound and separated using the chromatographic media herein. For example gold (Au), cadmium (Cd), zinc (Zn), cobalt (Co), titanium (Ti), nickel (Ni), palladium (Pd), and lead (Pb) can be bound using the methods described herein. These and other metals demonstrate different chemical properties and degrees of affinity to the selenolate-functionalized media.

The methods and resulting chromatographic media containing an appropriate choice of a selenium-functional group are further customized as useful for separating different metals and metal mixtures found in nature such as biological samples and environmental samples. The selenium-containing media are used individually or as a plurality of selenium-containing media (or with unmodified media), mixed in appropriate ratios to obtain a variety of affinity, separatory and retentive properties appropriate to the type of metal in a sample. The amount of selenium reacted to the stationary phase support medium, for example, silica gel, is optimized to afford the greatest extent of separation of the desired metal class or classes, for example a toxic metal, a composite metal, a high value metal, a transition metal, a lanthanide metal, and an actinide metal. In various embodiments compositions or chromatographic media containing selenium-functional groups (e.g., a selenol) is effective to scavenge or remove scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, actinium, rutherfordium, dubnium, seaborgium, bohrium, hassium, meitnerium, darmstadtium, or roentgenium.

The alkyl-selenium-silica gel medium provided herein was observed in Examples herein to have effectively separated a wide range of otherwise difficult to separate metals from organic molecules and their derivatives and analogs, including for example sterols, polyaromatic hydrocarbons, triglycerides, alkenes (olefins), alkanes, and alkenones, and inorganic compounds. The metal in various embodiments is scavenged, i.e. is removed from a reaction mixture, such that the metal removed is used as a catalyst to increase the rate of a reaction and to selectively produce a desired product. For example, the catalyst includes a metal catalyst for synthetic organic chemistry research and fine chemical production. For example, the catalyst is at least one of: a palladium for example palladium (II) acetate and allylchloro[1,3-bis(2,4,6-trimethylphenyl)imidazol-2-ylidene]palladium(II); a nickel for example bis(1,5-cyclooctadiene)nickel and dichloro[1,1'-bis(diphenylphosphino)ferrocene]nickel(II); a rhodium for example chloro(1,5-cyclooctadiene)rhodium(I) dimer; a ruthenium for example carbonylchlorohydridotris(triphenylphosphine)ruthenium(II) and 1-hydroxytetraphenylcyclopentadienyl(tetraphenyl-2,4-cyclopentadien-1-one)-μ-hydrotetracarbonyldiruthenium(II); a gold for example chloro[2-(di-t-butylphosphino)biphenyl]gold(I) and methyl(triphenylphosphine)gold(I); and a copper for example copper(II) trifluoromethanesulfonate and tetrakis(acetonitrile)copper(I) hexafluorophosphate. For example, the metal catalyst is used in a reaction such as a hydrogenation, a rearrangement, a carbonylation, an amination, an oxidation, a hydroboration, an epoxidation, a decarboxylation, a decarbonylation, a cyclization, a carbon-heteratom formation, or a carbon-carbon bond formation reaction (Fu, G. 2008 Acc. Chem. Res. 41: 1555-1564; Marion, N. et al. 2008 Acc. Chem. Res. 41: 1440-1449; Kantchev, E et al. 2007 Chem. Int. Ed. 6: 2768-2813; Martin, R. et al. 2008 Acc. Chem. Res. 41: 1461-1473; Knowles, J. P. et al. 2007 Org. Biomol. Chem. 5: 31-44; Falciola, C. A. et al. 2008 Eur. J. Org. Chem. 22: 3765-3780; Miyaura, N. 2002 Top. Curr. Chem. 219: 11-59; Espinet, P. et al. 2004 Chem. Int. Ed. 43: 4704-4734; Fugami, K. et al. 2002 Top. Curr. Chem. 219: 87-130; Valente, C. et al. 2012 Chem. Int. Ed. 51: 3314-3332; Knochel, P. et al. 2001 J. Org. Chem. 7: 1261-1277; Chincilla, R. et al. 2011 Chem. Soc. Rev. 40: 5084-5121; Surry, D. S. et al. 2011 Chem. Sci. 2: 27-50; Hartwig, J. F. 2008 Acc. Chem. Res. 41: 1534-1544; Evano, G. et al. 2008 Chem Rev. 108: 3054-3131; Negishi, E. (editor) Handbook on Organopalladium Chemistry for Organic Synthesis, volume 1, 2003 John Wiley & Sons; 3424 pages; and Hoff, R. et al. (editors) Handbook of Transition Metal Polymerization Catalysts, $1^{st}$ edition, Wiley Publishing, 575 pages, each of which is incorporated by reference herein in its entirety).

The medical field is increasingly interested in determining the number and kinds of molecules such as metals found in patient biological samples. Heavy metals may enter the body in food, water, or air, or by absorption through the skin. Once in the body, they compete with and displace essential minerals such as zinc, copper, magnesium, and calcium, and interfere with organ system function. People may contact heavy metals in industrial work, pharmaceutical manufacturing, and agriculture. Metal contamination (e.g., lead, cobalt, cadmium, arsenic, mercury, and thallium) of the environment has been observed to be widespread, and requires assays for monitoring extent of these metals in various parts of the environment and in subjects. Metals have been found to damage reproductive, renal, cardiovascular, and nervous systems, and many procedures have been developed to concentrate and analyze metals in serum and urine samples from mammals.

The compositions provided herein include at least one selenium-functional group, and are used in various embodiments as a component in a device or system to remove, bind, and/or concentrate the metals from or in these samples, such that, these metals subsequently can be identified and analyzed using techniques such as HPLC-MS.

Without being limited by any particular theory or mechanism of action, it is here envisioned that systems, methods, compositions and kits described herein using selenium-containing functional groups to effectively bind to and scavenge metal ions and compounds from aqueous solutions and reactions mixtures are useful in systems for analysis of other molecules which are of interest in medicine and environmental areas including carbohydrates, nucleic acids and proteins, and monomeric components such as sugars, amino acids, lipids, and include also synthetic polymers and monomeric components. The chromatographic compositions, methods, kits, and devices herein are useful for purification, isolation, and analysis of wide range of organic molecules and inorganic molecules remaining after metals are selectively removed.

The medium in various embodiments includes at least one selected from the group consisting of: silica, silica gel, alumina, polystyrene, agarose, modified polymeric resin, polymer fiber, cellulose, magnesium silicate, dextran, and starch. In a related embodiment, the medium is a substrate or nanoparticle that allows presentation of the selenium-containing functional group to selectively bind to the metal. In various embodiments, the medium includes at least one polymer that enhances a surface property of the medium. For example, the at least one polymer reduces non-specific binding of the selenium-containing functional group to non-metal components of the target. In a related embodiment, the polymer strengthens the medium against pressures encountered during binding of the metal to the selenium-containing functional group of the composition. See Grant et al., U.S. Pat. No. 7,335,306 issued Feb. 26, 2008; Sherrington et al., U.S. Pat. No. 7,332,086 issued Feb. 19, 2008; Burch et al., U.S. Pat. No. 7,250,388 issued Jul. 31, 2007; and Van Ness et al., U.S. Pat. No. 5,667,976 issued Sep. 16, 1997. In various embodiments, the medium or scaffold is cross-linked. See Kakodkar et al., U.S. Pat. No. 5,087,359 issued Feb. 11, 1992.

In various embodiments, the selenium-containing functional group is linked to the medium by at least one spacer selected from the group of: a sulfur-containing functional group: $(C_1-C_{30})$alkyl, $(C_1-C_{30})$alkynyl, $(C_3-C_{12})$carbocyclyl, $(C_1-C_{30})$alkoxy, $(C_1-C_{30})$heteroalkyl, $(C_6-C_{30})$aryl, $(C_1-C_{30})$heteroaryl, and $(C_6-C_{30})$aryl$(C_1-C_{30})$alkyl. For example, the selenium-containing functional group is linked to the medium by at least one spacer selected from the group consisting of: a sulfur-containing functional group: $(C_1-C_{18})$alkyl, $(C_1-C_{18})$alkoxy, $(C_1-C_{18})$heteroalkyl, $(C_6-C_{10})$aryl, $(C_1-C_9)$heteroaryl, and $(C_6-C_{10})$aryl$(C_1-C_6)$alkyl. For example, the spacer includes a carbocycle, a perhaloalkyl, an alkenyl, a heterocyclyl, a heteroaryl, a heteroaralkyl, a substituted amino (e.g., mono-substituted and di-substituted), a sulfonyl, a sulfinyl, an acyl, a boronyl, a propyl group, or a benzyl group. In various embodiments, the medium and/or the spacer comprises at least one protecting group.

The composition in various embodiments fours an analytical component of a chromatography system selected from: normal phase, reversed-phase, liquid, planar, column, flush, flash, thin layer, high performance liquid, gas, and solid phase extraction chromatography. The composition in a related embodiment forms a component of a dialysis system. In a related embodiment, the composition is used in an organic chemistry reaction scheme to remove the metal from a reagent and/or a product. For example, the composition is used to scavenge, recover, or remove a platinum catalyst or a rhodium catalyst. In various embodiments, the metal is a high value metal used in organic chemistry synthesis or cell culture processing.

Structural characteristics of organic molecules and inorganic molecules differ in affinities and specificities of binding to alkyl-selenium-metal chromatographic media provided herein compared to metals. The selenium-containing media described herein retain the metals and do not bind other molecules remaining in a suspension, solution, mixture or material. Hence methods herein involve affinity separations that selectively bind metals and recover the metals from wash solutions the target molecules or compounds at different times relative to the metals. Thus, in certain embodiments the selenium-containing functional group media are used to bind and remove metal impurities and other undesired metals found in natural samples and synthetic mixtures, and to recover these metals if further desired.

The chromatographic materials provided in examples herein are useful for a variety of products, and have wide application in different areas of organic chemistry such as environmental and pharmaceutical areas both for analytical and preparative chromatography. The selenium chromatographic media are useful in dialysis systems, solid phase extraction tubes, and in HPLC columns. For example, the dialysis system is a sterile system, and is used in hemodialysis, hemofiltration, hemodiafiltration, or peritoneal dialysis.

In hemodialysis and hemofiltration, blood from a subject is impelled to flow at a slow rate through a special filter that removes wastes and extra fluids. The filtered (i.e., clean) blood is then returned to the subject. Removal of the harmful wastes and extra salt and fluids from the blood helps to control blood pressure and to keep the proper balance of electrolytes such as potassium and sodium in the body (Handbook Of Dialysis, 4th edition, 2007, editors John T. Daugirdas, Peter Gerard Blake, Todd S. Ing, Lippincott Williams & Wilkins pages 1-774; Alam U.S. Pat. No. 8,012,350 issued Sep. 6, 2011; and Beiriger, U.S. Pat. No. 8,425,780 issued Apr. 23, 2013, each of which is incorporated by reference herein in its entirety). The dialysis system in various embodiments herein includes a device for delivering extracorporeal blood to a hemodialyzer, blood filter or dialysis assembly that uses a dialysis solution (dialysate) including at least one pump to filter and purify the blood of the subject. The dialysis system monitors and/or controls blood-flow rate, arterial pressure, venous pressure, and provides anticoagulant delivery. In various embodiments, an isotonic replacement fluid is added to the blood to replace fluid volume and electrolytes. In various embodiments, at least one therapeutic agent or replacement electrolyte is added to the blood after detoxification using the media provided herein, and prior to being re-introduced to the subject. The system in various embodiments further includes a user/machine interface operably connected to the system for delivering extracorporeal blood (Connell et al. U.S. Pat. No. 7,318,892 issued Jan. 15, 2008).

The selenium chromatographic media described in Examples herein are useful in peritoneal dialysis systems for treating subjects having conditions such as severe chronic kidney disease. Peritoneal dialysis in various embodiments uses a dialysis solution, also called dialysate, which is infused into a subject's peritoneal cavity using a device, e.g., a catheter or a syringe. In various embodiments, the dialysate is contacted to the peritoneal membrane of the peritoneal cavity (Ding et al., U.S. Pat. No. 8,404,091 issued Mar. 26, 2013). Waste, toxins and excess water pass from the patient's bloodstream, through the peritoneal membrane, and into the dialysate due to diffusion and osmosis, i.e., an osmotic gradient occurs across the membrane. The spent dialysate is drained from the subject in various embodiments, removing waste, toxins and excess water (Hopping et al., U.S. Pat. No. 8,403,880 issued Mar. 26, 2013).

In vivo microdialysis sampling, during which little or no fluid is removed from or introduced into the system, involves implanting a tubular dialysis membrane at the site of interest then continuously perfusing the interior of the membrane with a solution similar in composition to the body fluid at that site. The dialysate containing chemicals, ions, molecules or metals which diffuse through the membrane are collected and analyzed using electrophoresis, immunoblotting, ELISA, chromatography (e.g., HPLC and size-exclusion chromatography), mass spectrometry, or absorbance (Kissinger, U.S. Pat. No. 5,706,806 issued Jan. 13, 1998). For example, capillary electrophoresis is a technique used to analyze biological mixtures as a small volume of the sample in a capillary tube interior is required (Liao et al., U.S. Pat. No. 5,766,435 issued Jun. 16, 1998). Separations on extremely small volumes, and at high speeds are performed.

In various embodiments, a therapeutic agent added to blood after detoxification using dialysis, e.g., peritoneal dialysis. The therapeutic agent is added to the filtered fluid (e.g., blood) prior to re-introduction to the subject. In various embodiments, the therapeutic agent is selected from the group consisting of: anti-bacterial agent, anti-fungal agent, growth factors, anti-inflammatory agents, vasopressor agents including but not limited to nitric oxide and calcium channel blockers, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGFs), IGF binding proteins (IGFBPs), epidermal growth factor (EGF), platelet derived growth factor (PDGF), neu differentiation factor (NDF), hepatocyte growth factor (HGF), vascular endothelial growth factor (VEGF), heparin-binding EGF (HBEGF), thrombospondins, von Willebrand Factor-C, heparin and heparin sulfates, and hyaluronic acid. See Toole et al. U.S. Pat. No. 5,902,795 issued May 11, 1999, which is incorporated by reference herein in its entirety.

The therapeutic agent in various embodiments includes an anti-cancer or anti-tumor agent selected from the group of: alkylating agents, such as mechlorethamine, cyclophosphamide, melphalan, uracil mustard, chlorambucil, busulfan, carmustine, lomustine, semustine, streptozoticin, and decrabazine; antimetabolites, such as methotrexate, fluorouracil, fluorodeoxyuridine, cytarabine, azarabine, idoxuridine, mercaptopurine, azathioprine, thioguanine, and adenine arabinoside; natural product derivatives, such as irinotecan hydrochloride, vinblastine, vincristine, dactinomycin, daunorubicin, doxorubicin, mithramycin, taxanes (e.g., paclitaxel) bleomycin, etoposide, teniposide, and mitomycin C; and miscellaneous agents, such as hydroxyurea, procarbezine, mititane, and cisplatinum. See Brown et al. U.S. publication number 20050267069 published Dec. 1, 2005, which is incorporated by reference herein in its entirety.

In other embodiments, the therapeutic agent is a cell, a compound, a composition, biological or the like that potentiates, stabilizes or synergizes the effects of the modulator or another molecule or compound on a cell or tissue. In some embodiments, the drug may include without limitation anti-tumor, anti-viral, antibacterial, anti-mycobacterial, anti-fungal, anti-proliferative or anti-apoptotic agents. Drugs that are included in the compositions of the invention are well known in the art. See for example, Goodman & Gilman's The Pharmacological Basis of Therapeutics, 9th Ed., Hardman, et al., eds., McGraw-Hill, 1996, the contents of which are herein incorporated by reference herein.

Chromatographic media with a selenium-functional group provided herein are used in conjunction with various mass spectrometry methods such as electrospray ionization-mass spectrometry, for increased sensitivity for characterizing biomolecules, for example proteins and oligonucleotides as well as other high molecular weight compounds. Collisional induced dissociation methods have provided information on amino acid and nucleotide sequence and sites of damage or modification. Mass spectrometry has been more recently used for analysis of non-covalent complexes including oligonucleotide duplexes, quadruplexes, and DNA-protein complexes, and probing the higher order structure of proteins (Smith et al., U.S. Pat. No. 5,954,959 issued Sep. 21, 1999). Biological fluids contained in the extracellular spaces of living tissue, such as in the brain, other organs or subdermal tissue, often are sampled for research or diagnostic purposes. If sufficient fluid is available, it may be simply withdrawn and analyzed directly. However, in many embodiments, only small amounts of fluid are available and sampling is performed by indirect methods such as an ELISA, e.g., indirect fluorescent antibody (IFA) test. Thus, compositions and methods described herein are used for sensitive characterization of metals and biomolecules.

Solid phase extraction tubes (SPE) tubes are used widely in various embodiments for rapid, manual or automated separation of metals and/or metal classes for example metals having different atomic masses. The media provided herein are suitable for HPLC columns and are useful for chromatographic resolution of organic compounds and to separate metals in the sample. Resolution and speed of normal-phase and reversed-phase HPLC are improved by use of the media prepared by methods herein compared to prior normal-phase media that afford only limited separation of metals from organic products and inorganic products. Compositions and methods using SPE tubes having a selenium-functionalized media are used to separate metals and other molecules.

Chromatography is characterized by differing relative polarities of the mobile (liquid) and stationary (packing material) phases. Normal-phase chromatography involves a polar stationary phase, such as silanol on silica, and a relatively non-polar mobile phase, e.g., hexane and dichloromethane. Reversed-phase chromatography involves a non-polar stationary phase, often a hydrocarbon, and the mobile phase is relatively polar, e.g., water, methanol or acetonitrile. Generally in normal-phase chromatography, the least polar sample component is eluted first because it is most soluble in the non-polar mobile phase. Conversely, in reversed-phase chromatography, the most polar sample component is eluted first because it is most soluble in the polar mobile phase.

A selenol functionalized silica gel is used herein for reversed-phase chromatography separations. The procedures for making $C_{18}$ reversed-phase silica gel include imbedding the silver onto the silica gel thiol (3% to 5% surface coverage), and then covering the silica gel surface with $C_{18}$ alkyl chain molecules. More than 90% of pharmaceutical chromatographic separations are performed using reserved-phase chromatography. Selenium functionalized silica gels as described herein have a major application in reversed-phase chromatography and thin layer chromatography.

The term "spacer", as used herein refers to a chemical moiety used in chemistry synthesis to influence chemical properties, for example reaction conditions, molecule stability, steric hindrance, and hydrophobicity. A spacer for example is a single atom (e.g., a carbon or heteroatom) or an functional group (e.g., an alkyl group) situated between a plurality of atoms or functional groups, such that the carbons atoms create additional space between the plurality of atoms or functional groups, thus reducing repulsive interaction (i.e., steric hindrance) between the plurality of atoms and functions groups. The term spacer is used herein interchangeably with the term "linker".

The phrase "selenium-containing functional group", as used herein refers to a molecule or compound which has a molecular or compound structure that contains a selenium atom or selenium atom moiety. The selenium atom or moiety for example may have been attached by reaction with a functional group such as selenide, a selenol, or a selenolate.

The phrase "sulfur-containing functional group", as used herein refers to a molecule or compound which has a molecular or compound structure that contains a sulfur atom or sulfur atom moiety. The sulfur atom or moiety for example may have been attached by reaction with a functional group such as a thiol, a sulfide, and a disulfide. An exemplary "sulfur-containing functional group" is a thiol, however other sulfur containing functional groups are within the scope of the composition of the chromatographic media provided herein.

The term "derivative", as used herein refers to a chemically related form of a molecule or a compound having an additional substituent, for example, a different functional group or atom attached to an atom of the molecule.

The term "analog", as used herein refers to a chemically related form of a molecule or a compound having a different configuration, for example, an isomer, or a D-configuration rather than an L-configuration, or an molecule with the approximate size and shape of the molecule, or a molecule with modification to the atoms that are involved in a chemical bond, including for example to confer resistance to or to facilitate degradation, cleavage, addition, removal, and substitution.

The term "target", as used herein refers to a sample and its components, including a mixture, compound, solution, a colloid, suspension, gel, slurry, or solid having been exposed for containing or suspected of containing a metal or a plurality of metals. The selenium-containing media described herein is used to remove or scavenge the metal or plurality of the metals from the target. The media specifically bind to the metal and leave the remaining component(s) of the target within the sample. In various embodiments the target is a reaction mixture includes a catalyst. For example, the catalyst is a metal or metal compound. In a related embodiment, the target is a sample, mixture, compound, solution, suspension, gel, slurry, or solid at risk for exposure to or containing a metal or a plurality of metals. For example, the target is a biological sample from a subject having indicia/symptoms of metal poisoning.

In various embodiments, the target includes a polycyclic aromatic hydrocarbon, an alkene, an alkenone, a triglyceride, a monoglyceride, a diglyceride, a wax ester, a steryl ester, a phthalate, a sterol, a steroid, a terpene, a terpenoid, a tripemoid, a fatty acid, a lipid including a phospholipid and other complex lipid molecules, an oil, a sugar, an oligosaccharide, a polysaccharide, a carbohydrate, a protein, an amino acid, a fossil fuel, a natural or synthetic organic compound of pharmaceutical use, a petroleum-derived compound, a coal-derived compound, and a combination thereof found in a biological sample or an environmental sample.

The target in various embodiments includes a biological sample, for example from a subject such as a human or animal. In various embodiments the biological sample is at least one of: an excretion or a secretion such as tears, saliva, urine, feces, perspiration, blood, lymph, serum, plasma, cerebrospinal fluid, bile, semen, vaginal fluid, breast milk, and amniotic fluids.

For example the biological sample is from a plant, bacteria or archea, and is obtained by further separating techniques such as for example by solvent extraction. The target in various embodiments is an environmental sample for example: soil; water such as samples taken from a river, a glacier, an ocean and a lake; sediment; algal deposits; oil deposits; and fossil deposits including coal and tar, and atmospheric aerosols.

"Scavenging" as used herein refers to any salvaging, cleaning, or removing of a metal from an area, a solution, or a material. In certain embodiments scavenging involves, after contacting a target, further extracting, salvaging or separating a high value metal (e.g., gold and/or silver) from the target so as to recover the metal for further use. Alternatively, scavenging involves removing an unwanted metal from the target such that the target without the metal may be used. For example, scavenging in certain embodiments involves removing toxic metals, unwanted by-product metals, or catalyst metals from the target, such as from a pharmaceutical composition, a container, an aqueous layer, an organic layer, and a drinking-water source. In certain embodiments, the target includes an aqueous solution, suspension, or complex mixture. Scavenging includes without limitation removal of toxic metals from a patient by combining the media provided herein with standard blood dialysis procedures.

"Aqueous solution" as used herein pertains to or relates to a sample that is wholly or partially being dissolved in water. For example, the percent water in the aqueous solution is at least about 10%, at least about 20%, at least about 30%, at least about 40%, at least about 50%, at least about 60%, at least about 70%, at least about 75%, at least about 80%, at least about 90%, at least about 95%, or at least about 99% water. For example the aqueous solution is a water sample in need of determination of presence of one or more metals, or the aqueous solution is a previously used treatment fluid such as processing or cleaning water that is in need of treatment for compliance or disposal.

In various embodiments, the selenium-containing functional group is linked to the medium or the scaffold by at least one spacer selected from the group of: a sulfur-containing functional group: $(C_1$-$C_{30})$alkyl, $(C_1$-$C_{30})$alkynyl, $(C_3$-$C_{12})$carbocyclyl, $(C_1$-$C_{30})$alkoxy, $(C_1$-$C_{30})$heteroalkyl, $(C_6$-$C_{30})$aryl, $(C_1$-$C_{30})$heteroaryl, and $(C_6$-$C_{30})$aryl $(C_1$-$C_{30})$alkyl. For example, the selenium-containing functional group is linked to the medium by at least one spacer selected from the group consisting of: a sulfur-containing functional group: $(C_1$-$C_{18})$alkyl, $(C_1$-$C_{18})$alkoxy, $(C_1$-$C_{18})$heteroalkyl, $(C_6$-$C_{10})$aryl, $(C_1$-$C_9)$heteroaryl, and $(C_6$-$C_{10})$aryl$(C_1$-$C_6)$alkyl. For example, the spacer includes a carbocycle, a perhaloalkyl, an alkenyl, a heterocyclyl, a heteroaryl, a heteroaralkyl, a substituted amino (e.g., di-substituted and tri-substituted), a sulfonyl, a sulfinyl, an acyl, a boronyl, a propyl group, or a benzyl group. In various embodiments, the medium and/or the spacer comprises at least one protecting group. See Handbook of Chemistry and Physics, 94$^{th}$ edition, 2013; editor W. M. Haynes, Taylor and Francis Group Publishing, Boulder Colo.; Organic Chemistry, 1999, editor Thomas Sorrell, University Science Books, Sausalito; March's Advanced Organic Chemistry, 5th edition, 2001, editors Michael B. Smith et al., John Wiley & Sons, Inc., New York; Comprehensive Organic Transformations, 1989, author Richard C. Larock, VCH Publishers Inc., New York, N.Y.; and Modern Methods of Organic Synthesis, 4th Edition, 2004, authors William Carruthers et al., Cambridge University Press, Cambridge, UK, each of which is incorporated by reference herein in its entirety.

Examples herein show methods of preparing selenolate silica gels having a variety of linkers or spacers for attachment of the selenium functional group to the silica gel, for example a propyl (three carbons) group separating the silicon from the selenium respectively. The length of the aliphatic carbon chain alters the affinity properties of the silica. Accordingly, different functionalized silica gels are synthesized in examples herein by using as starting materials each of several different carbon spacer lengths, e.g., spacers having from 1 to 20 carbons. Possible spacers include alkyl and aryl structures and include heteroatoms and functional groups bonded to the carbon chains, for example oxygen, nitrogen, phosphorus, nitrile groups, di-thiol groups, thioester groups, carbonyl groups, and hydroxyl groups.

In various embodiments, the composition containing the selenium-containing functional group is disposable. Alternatively, the composition is re-usable. In various embodiments, the composition containing the selenium-containing functional group bound to the metal is treated to remove the bound metal. In various embodiments, the method involves applying a fluid or material that disrupts a complex or binding between the metal and the selenium functional group. For example the fluid or material includes at least one of an acid or an oxidizing agent. See Rosenberg et al., U.S. patent publication number 20040000523 published Jan. 1, 2004.

In various embodiments, removing the metal includes drying or heating the medium or the scaffold. In various embodiments, removing includes directing wavelengths of energy (e.g., microwaves and radiation) to the medium or the scaffold, or a using magnetic material (e.g., beads). In various embodiments, removing includes separating by size the metal and/or the other components of the target. In various embodiments, removing includes applying a flow of a fluid (e.g., a gas or a liquid). See Vladimir, U.S. Pat. No. 8,123,041 issued Feb. 28, 2012; Vorpahl, U.S. Pat. No. 5,770,388 issued Jun. 23, 1998; and Bai et al., U.S. patent publication number 20120272791 published Nov. 1, 2012, each of which is incorporated by reference herein in its entirety.

In various embodiments, after removing the metal, the composition is treated (i.e., regenerated or recharged), such that the composition can be re-used. For example regenerating or recharging the composition includes filtering, screening, heating, or drying. See Fortier et al., U.S. Pat. No. 6,248,683 issued Jun. 19, 2001.

In various embodiments of the method, the metal is a catalyst, and the method includes after removing, regenerating the metal catalyst. For example, the regenerating the metal catalyst includes using an adsorption medium or a complexing agent, for example an organo-complexing agent. In various embodiments, the complexing agent is selected from the group consisting of: an aliphatic and/or aromatic mono, di, and/or tribasic carboxylic acid, a polyacrylate, a polymethacrylate, a polyvinybenzoate, a polyvinylsulfate, a polyvinyl sulfonate, a polybiphenol carbonate, a polybenizimidazole, a polyvinylpyrrolidone, a polypyridine, an ethylene diaminc, a propylene diaminc, a diethylenetriamine, a triethylenetctraamine, a diethylenetriamine pentaccetic acid (DTPA), a N-Qiydroxyethyl)-ethylenediaminetriaccetic acid (HEDTA), an amino tri(methylanephosphonic acid) (ATMP), a 1-Hydroxy-1,1-diphosphonic acid (HEDP), a diethylenetriamine penta (methylphosphonic) acid, or a salt or combination thereof. See Zhou et al., U.S. Pat. No. 6,908,873 issued Jun. 21, 2005; and Sechrist, U.S. Pat. No. 6,790,802 issued Sep. 14, 2004. In general, the method described herein includes in various embodiments, after removing, analyzing for presence of the metal in the remaining material using instrumental analysis. See Skoog et al. 2006 Principles of Instrumental Analysis (sixth edition) Brooks Cole Publishing chapter 28.

In various embodiments, analyzing involves at least one technique or measurement selected from: spectrometry, absorbance, transmittance, and spectroscopy. For example, analyzing involves atomic absorption spectrometry, inductively coupled plasma mass spectrometry, anodic stripping voltammetry, X-ray fluorescence spectrometry, and microprobes. See Bannon, D. I. et al. 2001 Clin. Chem. 47 (9): 1703-1704; Liu, H. W. et al. 1999 Spectrochim. Acta, Part B 54 (9): 1367-1375; Yang, W. R. et al. 2003 Analyst 128 (6): 712-718; Baldo, M. A. et al. 2004 Electroanalysis 16 (5): 360-366; Eksperiandova, L. P. et al. 2002 X-ray Spectrom. 31 (3): 259-263; Arai, Y. et al. 2003 Environ. Sci. Technol. 37 (18): 4083-4090; Burdette, S. C. et al. 2003 J. Am. Chem. Soc. 2003, 125 (7), 1778-1787. Wu, X. Q. et al. 2000 Biotechnol. Prog. 16 (3): 513-516; Darwish, I. A. et al. 2002 Anal. Chem. 74 (1): 52-58; Godwin, H. 2000 J. Am. Chem. Soc. 122 (1): 174-175; Yang, W. R. et al. 2001 Chem. Commun. 19: 1982-1983; Shults, M. D. 2003 J. Am. Chem. Soc. 125 (35): 10591-10597; Mlynarz, P. et al. 2002 New J. Chem. 26 (2): 264-268; Shetty, R. S. et al. 2001 Abstr. Pap. Am. Chem. S. 221: U92-U92; Lu, Y. et al. 2003 Biosens. Bioelectron. 18 (5-6): 529-540; and Chinowsky, T. M. et al. 1996 Sens. Actuators B 35 (1-3): 37-43, each of which is incorporated by reference herein in its entirety.

Figure 1:
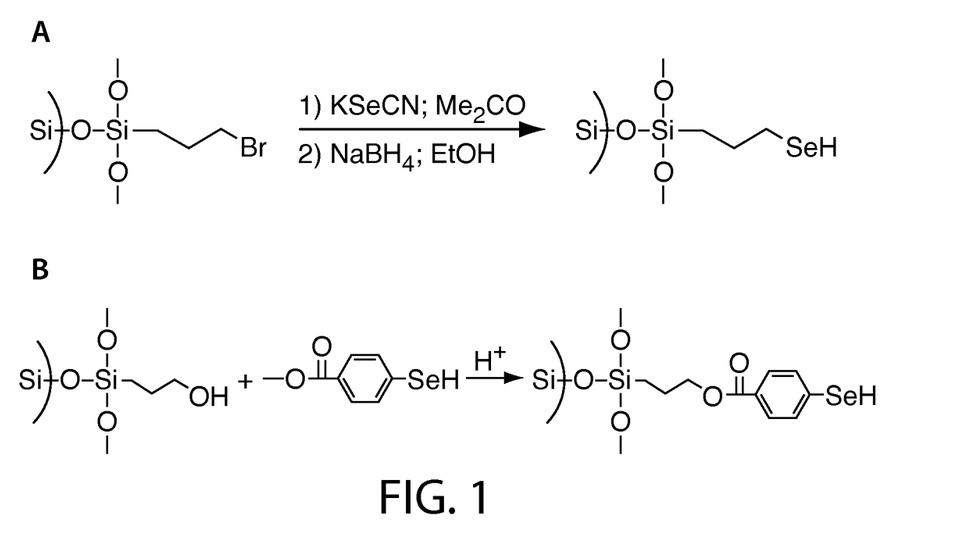
FIG. 1 is a drawing showing methods for preparing chromatographic media having a selenium-functional group.

Compositions, methods and kits are described herein for removing, recovering and/or scavenging a metal using a selenium-containing functional group attached or covalently linked to a medium, scaffold, or bead. In certain embodiments, the medium which may be considered to be a scaffold, or a bead, or a silica, for example as shown in FIG. 1 panels A-B and FIGS. 3-4.

The following examples and claims are illustrative and are not meant to be further limiting. Those skilled in the art will recognize or be able to ascertain using no more than routine experimentation, numerous equivalents to the specific procedures described herein. Such equivalents are within the scope of the present invention and claims. The contents of all references including issued patents, published patent applications and non-patent literature references cited in this application are hereby incorporated by reference herein in their entireties.

Examples

Example 1

Synthesis of a Propylselenol Trimethoxysilane

Organoselenium compounds form a more stable complex with silver (I) than organosulfur compounds (Pettit et. al. 1967 Chem. Commun. 1179-1180; and Kreif et al. 1985 Tetrahedron. 41(21): 4793-4812). Methods for preparing an organoselenium compound bound to silica surface that binds more effectively to metals than organosulfur compounds are illustrated in the Examples herein.

A 3-bromopropyltrimethoxysilane was reacted with potassium selenocyanate (KSeCN) in acetone and then reacted with sodium borohydride (NaBH$_4$) in ethanol to yield a propylselenol trimethoxysilane (FIG. 1 panel A).

The reactions shown in FIG. 1 panel A were performed by combining 3-bromopropyl functionalized silica (5.0 grams; g) and dimethylformamide (DMF; 30 milliliters) in a 250 mL three-necked flask fitted with a mechanical stirrer and a condenser. The solution was heated to 80° C. under an argon gas flow. Potassium selenium cyanide (1.42 g; approximately 1.4 molar equivalents) dissolved in DMF (30 milliliters; mL) was added slowly to the flask. The solution was stirred for four hours at 80° C. The resulting 3-seleniumcyanide-propyl functionalized silica was filtered using a vacuum filtration apparatus and was washed using three washes each of DMF and then methanol sequentially (50 mL per wash). The 3-seleniumcyanide-propyl functionalized silica was placed in a two-necked flask containing anhydrous dry ethanol (50 mL) and a mechanical stirrer. The silica was stirred and cooled to 0° C. Sodium borohydride (0.37 g; approximately molar 1.5 equivalents) in 30 mL of ethanol was added slowly to the flask and the solution was stirred for one hour at 0° C. The solution equilibrated to room temperature for one hour, and the solution was hydrolyzed three times using 10% aqueous hydrochloric acid solutions (15 mL each). The resulting 3-selenopropyl silica was filtered using a vacuum filter flask and was washed with water and ethanol sequentially (three washes each; 50 mL per wash). Elemental analysis of the reaction product shown in FIG. 1 panel A showed that the nitrogen content was not detected.

Example 2

Synthesis of a Benzylesterselenol Trimethoxysi Lane

Methods for synthesizing a benzylesterselenol trimethoxysilane are shown in Examples herein. The synthesis involves reacting 3-hydroxypropyltrimethoxysilane with a selenium benzyl ester under acidic conditions to yield 3-hydroxypropyltrimethoxysilane, a selenol silane with an aromatic ring (FIG. 1 panel B).

Figure 2:
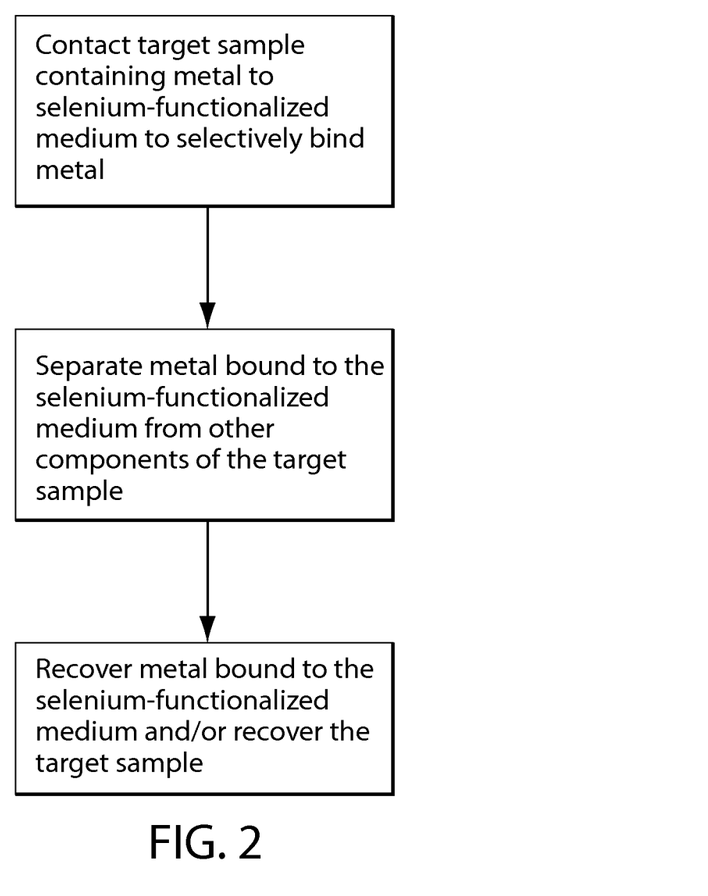
FIG. 2 is a drawing showing a system for recovering a metal from a target using a selenium-functionalized medium. The system involves contacting the target having a metal with a selenium functionalized medium (i.e., medium including a selenium-containing functional group) that specifically binds to the metal; separating the metal from the target having at least one remaining non-metal component; and recovering the metal from the medium and/or recovering the target including the at least one remaining non-metal component.

The reactions herein show multiple methods of preparing selenolate materials that effectively bind metals. The systems, methods, compositions and kits using selenium-containing functional groups effectively metal ions and compounds from a target (FIG. 2), for example the target includes an aqueous solution or a reaction mixture.

Chromatographic media including the selenium-containing functional groups described herein are stable during storage at temperatures below or at room temperature, and in the light and are reusable. Transition metals including platinum, nickel, gold and silver in solutions and mixtures are bound to the selenium containing functional groups on the medium. Separation components including selenolate chromatographic material produce accurate, reproducible and reliable separations, products and data for small-scale assays and diagnostic kits.

Example 3

Synthesis of a Selenoether Functionalized Silica

Figure 3:
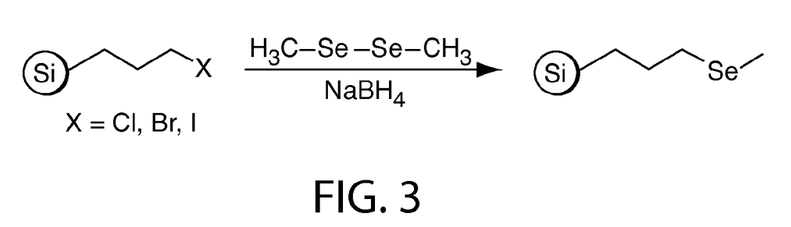
FIG. 3 is a drawing of a chemical reaction for synthesizing a selenoether functionalized silica material. The chemical reaction includes mixing a dimethyldiselenide with sodium borohydride, and adding the mixture in ethanol to a halogen-functionalized 3-propyl functionalized silica or silicon atom (X=chloride, Cl; bromide, Br; or iodide, I) to produce the selenoether functionalized silica material.
Figure 4:
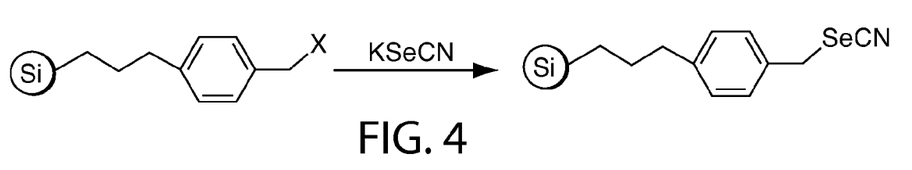
FIG. 4 is a drawing of a chemical reaction for synthesizing a benzylesterselenol functionalized silica material. The reaction is a nucleophilic substitution that reacts a potassium selenium cyanide to a halogenated 1-(chloromethyl)-4-propylbenzene functionalized silica or silicon atom.

Methods for synthesizing a selenoether functionalized silica are shown in FIG. 3. A solution of dimethyldiselenide (1.04 g, 5.5 millimoles) in 50 mL of ethanol was prepared and stirred at room temperature under a nitrogen gas flow. An aliquot of sodium borohydride (0.43 g, 11 millimoles) was added drop-wise to the solution and stirred for three hours. An amount of 3-propylchloride functionalized silica gel (4.65 g) was added to the solution and the resulting slurry was refluxed for 24 hours. The slurry was cooled, filtered and washed five times with 20 mL distilled water then rinsed three times with 20 mL ethanol. The slurry was dried under vacuum.

Example 4

Synthesis of a Benzylesterselenol Functionalized Silica

Methods are shown for synthesizing a silica having a benzyl moiety bound to a selenium functional group. Synthesis of a benzylesterselenol in FIG. 4 was performed by a nucleophilic substitution reaction. Potassium selenium cyanide was reacted with a halogenated 1-(halogen methyl)-4-propylbenzene functionalized silica.

Without being limited by any particular theory or mechanism of action, it is here envisioned that a methylene spacer could be chemically inserted between the selenium and the benzene in various embodiments to produce a functionalized silica that is effective to bind to and scavenge metal.

Example 5

Separation and Scavenging of Metals Using Selenium-Containing Chromatographic Material The selenium-functionalized media described herein are tested to determine ability to effectively scavenging and capturing transition metals that are used as catalyst during drug synthesis. Palladium is a common catalyst used for drug synthesis, and has been detected in trace amounts in products based on small-molecule active pharmaceutical ingredients (API).

The systems, methods, compositions and kits using the selenium-functionalized media described above are at least one order of magnitude more efficient on a weight basis, for recovering and extracting metals than thiol based silica gels. The selenium-functionalized media produces at least ten-fold less waste and is requires a ten-fold smaller volume, which is important for industrial metal scavenging facilities to process materials from a target material.

Further separations and scavenging analyses are performed with the selenium-functionalized media to determine the ability to scavenge transition metals such as platinum at different concentrations and percentages from a target. The compositions, methods and kit using the selenium-functionalized media are used to recover, separate, and/or scavenge platinum and transitions metals such as silver, palladium, nickel and gold from organic chemistry reaction mixtures and samples.

Example 6

Detection of Metals in Biological Samples Using a Device with a Selenium-Containing Functional Group Point-of-care devices and methods are shown herein for detecting presence of toxic heavy metals in biological samples from subjects. See Principles and Practice of Point-of-Care Testing (1st edition), 2002, editor Gerald J. Kost, publisher Lippincott Williams & Wilkins, pages 1-672, which is incorporated by references herein in its entirety.

A blinded study is performed using subjects from a population environmentally or industrially exposed to toxic heavy metals, and control subjects from a different population not exposed to the metals. Biological samples (i.e., urine and serum) are collected from the subjects and randomly assigned numbers such that subsequent testers using assay devices are unaware of presence or absence of the metals in samples, i.e., samples are analyzed by a double blind protocol.

Assay devices are prepared containing a housing which contains nitrocellulose media allowing for capillary action by the biological samples, a sample application area, a detection area, and a control area. Each sample is tested using an individual assay device. The sample is added to a sample application area having a gold labeled anti-human antibody. The sample flows over the nitrocellulose media to the detection area. The detection area contains a composition including a selenium-containing functional group which reacts and/or binds with the metal to form a visible band or mark. Control samples from subjects not exposed to metal are also analyzed by the devices.

The samples flows to a control area that is distal to detection the detection area, which identifies that the sample flowed through the test zone and thus is a control for the operation of the device. The control area in various embodiments includes an antibody that visibly detects a marker of the sample. The antibody in the control area binds to the marker that is bound to the gold-labeled anti-human antibody from the sample application area. For example, the antibody in the control area is an anti-human immunoglobulin produced by an animal host.

Data show that the assay devices are effective for detecting extremely small quantities of a toxic metal in a biological sample. The devices that analyze metal-containing biologically samples specifically bind the metal and provide highly efficient selectivity and sensitivity compared to other analyzed devices.

Example 7

Removal of Toxic Metals Using a Selenium-Containing Dialysis System

A dialysis system is used to determine whether the selenium-functionalized medium is effective to bind and remove metals from a biological sample circulating from and to a living subject. The system includes a needle for obtaining blood from the subject. The system includes monitors for calculated the subject's temperature, blood pressure and heart rate prior to, during and after the dialysis procedure (Handbook Of Dialysis, 4th edition, 2007, editors John T. Daugirdas et al., Lippincott Williams & Wilkins Publishing, pages 1-774, which is incorporated by reference herein in its entirety).

The needle is connected to an inlet tube. The inlet tube transmits the samples from the needle to a proximal end of a dialysis assembly including a porous membrane and an atoxic selenium-functionalized media for binding a metal in the sample. The blood is introduced into the dialysis assembly using a pump lying between the needle and the dialysis assembly. A dialysis buffer is applied to the membrane with the selenium-functional group containing medium in the dialysis assembly and outside the membrane, to facilitate removal of metal contaminants and solutes that are at an undesirable concentration. The distal end of the dialysis assembly includes an outlet tube that takes the dialyzed blood from which the metal contaminants have been removed to be re-introduced into the subject.

Data show that the dialysis assembly having the membrane and the selenium-functionalized media is effective for selectively removing toxic materials and metals, and excess water from the blood in subjects having conditions such as renal failure caused by uremia or acidemia.

What is claimed is:

1. A method for recovering, removing, or scavenging a metal from a target, the method comprising:

contacting the target containing the metal with a medium or a scaffold comprising a selenium-containing functional group which is linked to the medium by a sulfur-containing functional group selected from a thiol or a thiolate, whereby the selenium-containing functional group specifically binds to the metal and separates the metal from at least one remaining component in the target; and, separating the medium or the scaffold from the target, wherein the target is a material selected from the group comprising of: an aqueous material, a reaction mixture, a complex material, and a biological sample.

2. The method according to claim 1, wherein the metal is selected from the group comprising of: a toxic metal, a composite metal, a high value metal, a transition metal, a lanthanide metal, and an actinide metal, for example the metal is at least one selected from the group of: scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, actinium, rutherfordium, dubnium, seaborgium, bohrium, hassium, meitnerium, darmstadtium, and roentgenium.

3. The method according to claim 1, wherein the medium or the scaffold comprises silica or is covalently linked or immobilized to the selenium-containing functional group by at least one spacer wherein the spacer is selected from the group consisting of: $(C_1-C_{18})$alkyl, $(C_1-C_8)$alkoxy, $(C_1-C_8)$heteroalkyl, $(C_6-C_{10})$aryl, $(C_1-C_9)$heteroaryl, and $(C_6-C_{10})$aryl$(C_1-C_6)$alkyl.

4. The method according to claim 1, wherein contacting further comprises at least one step selected from the group of: stirring, sonicating, and filtering.

5. The method according to claim 1, wherein, after contacting, the method further comprises washing or drying a resulting solid.

6. The method according to claim 1, wherein the contacting comprises adding at least one solvent selected from the group consisting of: chloroform, dichloromethane, ethyl acetate, diethyl ether, acetic acid, hexane, toluene, ethanol, acetone, methanol, tetrahydrofuran, dimethyl sulfoxide, acetonitrile, and a combination thereof.

7. The method according to claim 1, wherein prior to contacting, the method comprises reacting a selenium benzyl ester with at least one silane selected from the group comprising of: 3-mercaptopropyltrimethoxysilane, 3-hydroxypropyltrimethoxysilane, 3-glycidoxypropyltrimethoxysilane, n-butyltrimethoxysilane, and 3-cyanopropyltrimethoxysilane to form the resulting selenium containing functional group.

8. The method according to claim 1, wherein the medium comprises an activated silica gel or the medium is selected from the group consisting of: silica, silica gel, an activated silica gel, alumina, polystyrene, agarose, modified polymeric resin, cellulose, magnesium silicate, dextran, and starch.

* * * * *

UNITED STATES PATENT AND TRADEMARK OFFICE
CERTIFICATE OF CORRECTION

PATENT NO.       : 9,586,192 B2  
APPLICATION NO.  : 14/600296  
DATED            : March 7, 2017  
INVENTOR(S)      : Huang et al.

Page 1 of 1

It is certified that error appears in the above-identified patent and that said Letters Patent is hereby corrected as shown below:

In Claim 3, Column 30, Line 1:  
Delete "group consisting of: $(C_1-C_{18})$alkyl, $(C_1-C_8)$alkoxy, $(C_1-C_8)$"  
Insert --group consisting of: $(C_1-C_{18})$alkyl, $(C_1-C_{18})$alkoxy, $(C_1-C_{18})$--

Signed and Sealed this  
Twenty-third Day of May, 2017

Michelle K. Lee  
*Director of the United States Patent and Trademark Office*